US010568627B2

(12) United States Patent
Guo et al.

(10) Patent No.: US 10,568,627 B2
(45) Date of Patent: Feb. 25, 2020

(54) SURGICAL FASTENERS FOR MESH AND TISSUE FIXATION

(71) Applicant: Ethicon, Inc., Somerville, NJ (US)

(72) Inventors: Jianxin Guo, Livingston, NJ (US); Simon Cohn, Lebanon, NJ (US); Michael Cardinale, Morristown, NJ (US); Doug Souls, Andover, NJ (US); Jephté Augustin, Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 111 days.

(21) Appl. No.: 15/372,241

(22) Filed: Dec. 7, 2016

(65) Prior Publication Data

US 2018/0153551 A1    Jun. 7, 2018

(51) Int. Cl.
| | | |
|---|---|---|
| *A61B 17/08* | (2006.01) | |
| *A61B 17/10* | (2006.01) | |
| *A61B 17/072* | (2006.01) | |
| *A61B 17/064* | (2006.01) | |
| *A61B 17/068* | (2006.01) | |

(52) U.S. Cl.
CPC .......... *A61B 17/08* (2013.01); *A61B 17/064* (2013.01); *A61B 17/0682* (2013.01); *A61B 17/10* (2013.01)

(58) Field of Classification Search
CPC ... A61B 17/08; A61B 17/064; A61B 17/0644; A61B 17/0682; A61B 17/072; A61B 17/10
See application file for complete search history.

(56) References Cited

U.S. PATENT DOCUMENTS

| | | |
|---|---|---|
| 3,740,994 A | 6/1973 | DeCarlo |
| 4,325,376 A | 4/1982 | Klieman et al. |
| 4,471,780 A | 9/1984 | Menges et al. |
| 4,478,220 A | 10/1984 | DiGiovanni et al. |
| D286,180 S | 10/1986 | Korthoff |
| D286,442 S | 10/1986 | Korthoff |
| 4,724,839 A | 2/1988 | Bedi et al. |

(Continued)

FOREIGN PATENT DOCUMENTS

| | | |
|---|---|---|
| CA | 2464287 | 5/2003 |
| WO | 2013009993 | 1/2013 |
| WO | 2016007626 | 1/2016 |

OTHER PUBLICATIONS

International Search Report issued in corresponding International Application No. PCT/US2017/061286, dated Jun. 25, 2018, 5 pages.

*Primary Examiner* — Tuan V Nguyen

(57) ABSTRACT

A surgical fastener includes a first leg having a first distal barb and a first proximal barb that extend inwardly, and a second leg having a second distal barb and a second proximal barb that extend inwardly. A bridge interconnects proximal ends of the first and second legs. A first distance between opposing inner tips of the first and second distal barbs is greater than a second distance between opposing inner tips of the first and second proximal barbs. The first leg tapers inwardly between the proximal and distal ends thereof and has a cross-sectional area that is greater at the proximal end than at the distal end. The second leg tapers inwardly between the proximal and distal ends thereof and has a cross-sectional area that is greater at the proximal end than at the distal end. An insertion tool engages a crown on the proximal side of the bridge.

19 Claims, 26 Drawing Sheets

(56) References Cited

U.S. PATENT DOCUMENTS

| | | | |
|---|---|---|---|
| 4,932,960 A * | 6/1990 | Green | A61B 17/0643 606/220 |
| 5,203,864 A | 4/1993 | Phillips | |
| 5,290,297 A | 3/1994 | Phillips | |
| 5,470,010 A | 11/1995 | Rothfuss et al. | |
| 5,582,616 A | 12/1996 | Bolduc et al. | |
| 5,601,573 A | 2/1997 | Fogelberg et al. | |
| 5,810,882 A | 9/1998 | Bolduc et al. | |
| 5,830,221 A | 11/1998 | Stein et al. | |
| 5,833,700 A | 11/1998 | Fogelberg et al. | |
| 5,921,997 A | 7/1999 | Fogelberg et al. | |
| 7,722,610 B2 | 5/2010 | Viola | |
| 8,579,920 B2 | 11/2013 | Nering et al. | |
| 8,728,098 B2 | 5/2014 | Daniel et al. | |
| 8,728,099 B2 | 5/2014 | Cohn et al. | |
| 8,740,919 B2 | 6/2014 | Straehnz | |
| 8,894,669 B2 | 11/2014 | Nering et al. | |
| 8,920,439 B2 | 12/2014 | Cardinale et al. | |
| 9,055,945 B2 | 6/2015 | Miksza et al. | |
| 9,119,617 B2 | 9/2015 | Souls | |
| D744,646 S | 12/2015 | Nering et al. | |
| 9,675,395 B2 | 6/2017 | Averous | |
| D804,666 S | 12/2017 | Guo et al. | |
| 2002/0019636 A1 * | 2/2002 | Ogilvie | A61B 17/0642 606/75 |
| 2002/0068947 A1 | 6/2002 | Kuhns et al. | |
| 2005/0273108 A1 * | 12/2005 | Groiso | A61B 17/0642 606/75 |
| 2007/0162030 A1 * | 7/2007 | Aranyi | A61B 17/064 606/75 |
| 2007/0239278 A1 * | 10/2007 | Heinz | A61F 2/4425 623/17.15 |
| 2008/0065153 A1 | 3/2008 | Allard | |
| 2010/0292712 A1 | 11/2010 | Nering et al. | |
| 2014/0276968 A1 | 9/2014 | Miksza | |
| 2015/0080919 A1 | 3/2015 | Nering et al. | |

* cited by examiner

SURGICAL FASTENERS FOR MESH AND TISSUE FIXATION

CROSS-REFERENCE TO RELATED APPLICATIONS

The present patent application is related to U.S. Provisional Ser. No. 62/431,355, entitled "APPLICATOR INSTRUMENTS FOR DISPENSING SURGICAL FASTENERS," filed on even date herewith, the disclosure of which is hereby incorporated by reference herein.

BACKGROUND OF THE INVENTION

Field of the Invention

The present patent application generally relates to medical devices and surgical procedures, and more specifically relates to surgical fasteners used to secure tissue and for securing prosthetic devices to tissue.

Description of the Related Art

Hernia is a condition where a small loop of bowel or intestine protrudes through a weak place or defect within the abdominal muscle wall or groin of a patient. This condition commonly occurs in humans, particularly males. Hernias of this type may result from a congenital defect whereby the patient is born with this problem, or may be caused by straining or lifting heavy objects. Heavy lifting may be known to create a large amount of stress upon the abdominal wall and can cause a rupture or tearing at a weak point of the abdominal muscle to create the defect or opening. In any case, the patient may be left with an unsightly bulge of intestinal tissue protruding through the defect, which may result in pain, reduced lifting abilities, and in some cases, impaction of the bowel, or possibly other complications if the flow of blood is cut off to the protruding tissue.

A common solution to the above-described problem may be surgery. During a surgical procedure, the defect is accessed and carefully examined, either through an open incision or endoscopically through an access port such as a trocar. In either case, careful examination is required due to the network of vessels and nerves which exist in the area of a typical defect, which requires a surgeon to conduct a hernia repair with great skill and caution. Within this area can be found vascular structures such as gastric vessels, the external iliac vessels, and the inferior epigastric vessels, as well as reproductive vessels such as the vas deferens extending through the inguinal floor.

Once the surgeon is familiar with the anatomy of a patient, the surgeon carefully places the viscera back into the patient's abdomen through the defect. Repairing the defect can involve closure of the defect with sutures or fasteners but generally involves placing a surgical prosthetic such as a mesh patch over the open defect, and attaching the mesh patch to the abdominal wall or inguinal floor with conventional suture or with surgical fasteners. The mesh patch acts as a barrier and prevents expulsion of bowel through the defect. Suturing of the mesh patch to the inguinal floor can be well suited to open procedures but can be much more difficult and time consuming with endoscopic procedures. With the adoption of endoscopic surgery, endoscopic surgical instruments that apply surgical fasteners can be used. However, the tissue of the inguinal floor may offer special challenges to the surgeon when a needle or fastener is used to penetrate structures such as Cooper's ligament.

At present, there are a variety of surgical instruments and fasteners available for the surgeon to use in an endoscopic or open procedure to attach the mesh patch to the inguinal floor. One of the earliest types of endoscopic surgical instruments used is a surgical stapler. A plurality or stack of these unformed staples may be generally contained within a stapling cartridge in a serial fashion, and may be sequentially advanced or fed within the instrument by a spring mechanism. A secondary valving or feeding mechanism may be employed to separate the distal most staple from the stack, to hold the remainder of the spring loaded stack, and may be used to feed the distal most staples into the staple forming mechanism. Feeding mechanisms of this type are found in U.S. Pat. No. 5,470,010 to Rothfuss et al., and in U.S. Pat. No. 5,582,616, also to Rothfuss et al.

Another hernia mesh attachment instrument uses a helical wire fastener that resembles a small section of spring. Multiple helical wire fasteners may be stored serially within the 5 mm shaft, and may be corkscrewed or rotated into tissue. A load spring may be used to bias or feed the plurality of helical fasteners distally within the shaft. A protrusion extends into the shaft to possibly prevent the ejection of the stack of fasteners by the load spring and may permit passage of a rotating fastener. Instruments and fasteners of these types are found in U.S. Pat. No. 5,582,616 to Bolduc et al., U.S. Pat. No. 5,810,882 to Bolduc et al., and in U.S. Pat. No. 5,830,221 to Stein et al.

Whereas the above surgical instruments may be used for hernia fastening applications, they use a spring mechanism to feed a plurality of fasteners through the surgical instrument. Spring mechanisms typically use a long soft coil spring to push a stack of fasteners through a guide or track within the shaft of the surgical instrument. These types of feeding mechanisms may be generally simple and reliable, but may require an additional secondary valving mechanism or protrusion to separate and feed one fastener from the stack.

Other surgical fasteners may be used for hernia mesh attachment but utilize either a reloadable single shot instrument or a rotary magazine that holds a small number of fasteners. These types of surgical fastening instruments can be found in U.S. Pat. Nos. 5,203,864 and 5,290,297, both to Edward Phillips. These instruments have not gained acceptance by the surgical community, possibly due to their single shot capabilities and the large size of the rotary magazine, which can restrict such an instrument to an open procedure.

Whereas all the above surgical instruments may be used for hernia fastening applications, they either use a spring mechanism to feed the plurality of fasteners through the surgical instrument, or a rotary magazine in lieu of a feeding mechanism. Other types of surgical fasteners may be available, such as surgical clips, and they can utilize feeding mechanisms that do not require the use of a spring to feed the clips distally. A reciprocating feeding mechanism is described in U.S. Pat. Nos. 5,601,573; 5,833,700; and 5,921,997 to Fogelberg et al. The Fogelberg et al. references teach a clip applier with a feeding mechanism that utilizes a reciprocating feed bar to feed a serial stack of clips. A feeder shoe may operably engage with and move with the distally moving feed bar and may slidingly engage with the proximally moving feed bar. Thus, the feeder shoe may index or push the stack of clips distally with the distally moving feed bar and remains stationary relative to the proximally moving feed bar. A valving mechanism may be also required to separate the distal-most clip from the stack and to hold the stack stationary as the distal most clip may be applied onto a vessel. Whereas the Fogelberg et al. references teach a reciprocating feeding mechanism with a single reciprocating member, they do not teach the use of the clip applier in the attachment of hernia mesh, nor do they teach the individual driving or feeding of each clip by a moving member.

Another fastener feeding mechanism that uses reciprocation is that disclosed in U.S. Pat. No. 4,325,376 to Klieman et al. A clip applier that stores a plurality of clips in a serial fashion within a clip magazine is disclosed. The clips are in a stack wherein the proximal-most clip may be pushed or fed distally by a pawl that may be ratcheted or indexed distally by a reciprocating member or ratchet blade with each actuation of the instrument. As the pawl indexes distally, it can push the stack of clips distally. A secondary valving mechanism may be also described. Thus, the feeding mechanism of Klieman et al. teaches the use a single reciprocating member and pawl to push or feed the stack of clips distally, and may require a secondary valving mechanism to feed the distal most clip.

U.S. Pat. No. 3,740,994 to DeCarlo Jr. discloses a reciprocating feeding mechanism that indexes a plurality of staples or clips, and readies them for discharge by reciprocating one of a pair of opposing leaf spring assemblies. The staples reside serially within a guide rail with a fixed leaf spring assembly extending into the plane of the guide rail. A reciprocating leaf spring assembly extends inwardly towards the fixed leaf spring assembly. As the reciprocating leaf spring assembly moves distally, each of individual leaf springs of the assembly may engage a staple and move it distally. The distally moving staples deflect the local individual leaf springs of the fixed leaf spring assembly, and the deflected leaf springs may return to the un-deflected position after passage of the staple. As the moving leaf spring assembly moves proximally, the leaf springs of the fixed leaf spring assembly hold the staples stationary and prevent proximal movement thereof. A secondary guide rail and valving mechanism may be provided to separate a single staple from the stack for forming and can hold the stack of staples stationary as the single clip is formed.

Additionally, similar feeding mechanisms are disclosed in U.S. Pat. No. 4,478,220 to DiGiovanni et al. and U.S. Pat. No. 4,471,780 to Menges et al. Both of these related patents teach a reciprocating feeding mechanism that uses one fixed member and one reciprocating member to feed or index a plurality of clips distally. Angled flexible fingers may be hingedly attached to the reciprocating member and operatively engage the clips when moving distally, and slidingly engage with the clips when moving proximally. The angled flexible fingers within the fixed member deflect out of the way when the clips move distally and spring up to stop proximal movement of the clip after the clip has passed. A secondary valving mechanism is also disclosed.

Commonly assigned U.S. Patent Application Publication No. 2002/0068947, the disclosure of which is hereby incorporated by reference herein, teaches a device for delivering a plurality of individual surgical fasteners. In one embodiment, the delivery device includes a drive mechanism having distal and proximal ends. The drive mechanism has a moving member and a fixed opposing member, whereby the moving member is moveable proximally and distally with respect to the delivery device. The moving member has a sharpened distal end for piercing tissue. The device includes at least one surgical fastener located between the first and the second members. Each of the at least one surgical fasteners has a proximal end and a distal end. The device also has an actuator having at least two sequential positions. A first position for moving the moving member distally and piercing tissue, and a second position for moving the moving member proximally, thereby deploying the distal end of the fastener.

Commonly assigned U.S. Pat. Nos. 8,579,920; 8,728,098; 8,728,099; 8,894,669; and 8,920,439, disclose applicator instruments that contain a plurality of surgical fasteners. In one embodiment, an applicator instrument includes a plurality of surgical fasteners stored in series along the length of an elongated shaft having a pair of flat stampings having tabbed features incorporated therein. One of the flat stampings is stationary for preventing the surgical fasteners from moving proximally within the articulating shaft, and the other flat stamping cycles in distal and proximal directions each time a trigger is squeezed and then released to facilitate incremental advancement of the surgical fasteners along the length of the shaft. In one embodiment, a lead surgical fastener is staged for firing proximal by piloting a firing rod into the lead fastener and delivering the surgical fastener through a surgical fastener dispensing window at the distal end of the elongated shaft. The stampings may be flexible so that the stampings may curve to conform to the angle of an articulating shaft while guiding the surgical fasteners along the path defined by the shaft. In one embodiment, a single, lead surgical fastener is dispensed each time the trigger is pulled. During each trigger pull, each of the trailing surgical fasteners are advanced distally toward the distal end of the articulating shaft.

Tacks for fixing meshes used laparoscopically have generally been made of metal, such as stainless steel, nitinol, or titanium. The metal tacks were necessary to provide for sufficient holding strength, penetration of various prosthetic meshes, and for ease of manufacture. Until recently, there were no absorbable tacks available on the market, and surgeons could only use absorbable sutures in order to provide a fixation means that did not permanently stay in the body. However, using sutures is exceedingly difficult for laparoscopic procedure, and so they are generally not used unless the repair is done in an open fashion. With surgical trends leading to more minimally invasive techniques with minimum foreign body accumulation, an absorbable tack with minimum profile that can be applied laparoscopically is needed.

U.S. Pat. No. 8,894,669, assigned to Ethicon, Inc. of Somerville, N.J., discloses a surgical fastener having a first leg including a distal end, a proximal end, and a first insertion tip at the distal end of the first leg, the first insertion tip having a first distal piercing point, and a second leg including a distal end, a proximal end, and a second insertion tip at the distal end of the second leg, the second insertion tip having a second distal piercing point. The surgical fastener includes a bridge connecting the proximal ends of the first and second legs for forming a closed end of the surgical fastener. The first insertion tip has a first insertion tool seating surface, and the second insertion tip has a second insertion tool seating surface. The first and second distal piercing points are located outside the respective first and second legs. The first and second legs have outer walls that face away from one another in opposite directions, and the distance between the first and second distal piercing points is greater than the distance between the outer walls of the first and second legs that face away from one another in opposite directions. The first and second legs extend along respective longitudinal axes, and the first and second insertion tips are asymmetrical and skewed outwardly relative to the respective longitudinal axes of the first and second legs.

U.S. Pat. No. 9,055,945, assigned to Ethicon, Inc. of Somerville, N.J., discloses a surgical fastener having a first leg including a proximal end, a distal end, a first insertion tip at the distal end of the first leg, the first insertion tip having a length, and a first articulating joint that separates the first leg into a proximal segment and a distal segment that is deflectable relative to the proximal segment of the first leg. The surgical fastener has a second leg including a proximal end, a distal end, a second insertion tip at the distal end of the second leg, the second insertion tip having a length, and a second articulating joint that separates the second leg into a proximal segment and a distal segment that is deflectable relative to the proximal segment of the second leg. The first and second insertion tips are asymmetrical and skewed outwardly relative to respective longitudinal axes of the first and second legs in both an undeflected and deflected state. A bridge connects the proximal ends of the first and second legs for forming a closed end of the surgical fastener.

In spite of the above advances, there remains a need for further improvements. In particular, there remains a need for surgical fasteners having a minimum profile, that may be applied laparoscopically, that are absorbable, that provide enhanced tissue gripping, that are easy to orient and stabilize, and that minimize bleeding and recovery time.

SUMMARY OF THE INVENTION

In one embodiment, a surgical fastener preferably includes a first leg having a proximal end, a distal end, a first longitudinal axis that extends between the proximal and distal ends of the first leg, and at least one barb extending from the first leg. The surgical fastener desirably has a second leg including a proximal end, a distal end, a second longitudinal axis that extends between the proximal and distal ends of the second leg, and at least one barb extending from the second leg. In one embodiment, a bridge interconnects the proximal ends of the first and second legs.

In one embodiment, the first leg has a cross-sectional area that is greater at the proximal end than at the distal end thereof, and the second leg has a cross-sectional area that is greater at the proximal end than at the distal end thereof. In one embodiment, the first leg tapers inwardly between the proximal and distal ends thereof, and the second leg tapers inwardly between the proximal and distal ends thereof.

In one embodiment, the cross-sectional areas of the first and second legs at the proximal ends of the respective first and second legs define convex surfaces or cylindrical shapes adapted for plugging entrance holes created by the distal ends of the first and second legs for preventing or reducing bleeding from the entrance holes. In one embodiment, the cross-sectional shapes of the legs at the proximal ends of the legs defines shapes that are designed to effectively plug the holes or tissue openings formed by the distal tips of the legs for preventing or minimizing bleeding from the holes.

In one embodiment, the at least one barb on the first leg extends inwardly toward the second leg, and the at least one barb on the second leg extends inwardly toward the first leg. In one embodiment, the at least one barb on the first leg includes a first distal barb extending inwardly from the distal end of the first leg and a first proximal barb extending inwardly from a location on the first leg that is proximal to the first distal barb. In one embodiment, the at least one barb on the second leg includes a second distal barb extending inwardly from the distal end of the second leg and a second proximal barb extending inwardly from a location on the first leg that is proximal to the second distal barb.

In one embodiment, the barbs on the first leg have respective thicknesses that are less than the thickness or diameter of the first leg, and the barbs on the second leg have respective thicknesses that are less than the thickness or diameter of the second leg.

In one embodiment, a first distance between an inner tip of the first distal barb and an inner tip of the second distal barb is greater than a second distance between an inner tip of the first proximal barb and an inner tip of the second proximal barb. In one embodiment, the first distance between the first and second distal barbs is about 0.030 inches and the second distance between the first and second proximal barbs is about 0.040 inches.

In one embodiment, the distal ends of the first and second legs are advanced into tissue followed by the first and second distal barbs, which forms two spaced tissue openings. In one embodiment, the two tissue openings will be about 0.040 inches away from one another, which is equal to the distance between the inner tips of the first and second distal barbs. In one embodiment, the first and second proximal barbs are closer together than are the first and second distal barbs, which enables the first and second proximal barbs to better grip or bite into the side walls of the tissue openings previously formed by the first and second distal barbs.

In one embodiment, the first and second distal barbs extend inwardly toward one another and are aligned with one another along the respective longitudinal axes of the first and second legs. In one embodiment, the first and second proximal barbs extend inwardly toward one another and are aligned with one another along the respective longitudinal axes of the first and second legs.

In one embodiment, the distal end of the first leg includes a first insertion tip having a first distal piercing point and the distal end of the second leg includes a second insertion tip having a second distal piercing point. In one embodiment, the first and second insertion tips are asymmetrical. In one embodiment, the first distal barb extends inwardly from the first insertion tip and the second distal barb extends inwardly from the second insertion tip.

In one embodiment, the first leg has a first outer wall that extends from a first end of the bridge to the first distal piercing point, and the second leg has a second outer wall that extends from a second end of the bridge to the second distal piercing point. In one embodiment, the distance between the first and second outer walls defines a width of the surgical fastener that remains constant between the first and second ends of the bridge and the first and second distal piercing points.

In one embodiment, the bridge extends along a proximal end of the surgical fastener, and the surgical fastener has a width that remains constant between the bridge and the distal ends of the first and second legs.

In one embodiment, the bridge has a length that defines the width of the surgical fastener at the proximal end of the surgical fastener.

In one embodiment, the bridge includes a major surface that faces away from the distal ends of the first and second legs, and a crown that extends proximally from the major surface of the bridge. In one embodiment, the crown has a cruciform shape including a center section that is centered on the major surface of the bridge and first and second flanges that extend laterally from opposite sides of the center section.

In one embodiment, the major surface of the bridge includes a first C-shaped section that surrounds the first flange, and a second C-shaped section that opposes the first C-shaped section and that surrounds the second flange.

In one embodiment, a system for dispensing a surgical fastener includes an insertion tool having a distal end with a distal face and first and second C-shaped projections on opposite ends of the distal face that oppose one another and that extend distally from the distal face. In one embodiment, the first C-shaped projection engages the first C-shaped section of the major face that surrounds the first flange of the crown, the second C-shaped projection engages the second C-shaped section of the major face that surrounds the second flange of the crown, and the center section of the crown is disposed between the first and second C-shaped projections.

In one embodiment, the crown defines a first height relative to the major surface of the bridge and the C-shaped projections define a second height relative to the distal face of the insertion tool that is greater than the first height. In one embodiment, when the C-shaped projections of the insertion tool engage the first and second C-shaped sections of the major face, the distal face of the insertion tool is spaced away from the crown.

In one embodiment, a surgical fastener includes a first leg with a proximal end, a distal end, a first longitudinal axis that extends between the proximal and distal ends of the first leg, a first distal barb extending inwardly from the distal end of the first leg, and a first proximal barb extending inwardly from a location on the first leg that is proximal to the first distal barb. In one embodiment, the surgical fastener includes a second leg with a proximal end, a distal end, a second longitudinal axis that extends between the proximal and distal ends of the second leg, a second distal barb extending inwardly from the distal end of the second leg, and a second proximal barb extending inwardly from a location on the first leg that is proximal to the second distal barb. A bridge preferably interconnects the proximal ends of the first and second legs.

In one embodiment, a first distance between an inner tip of the first distal barb and an inner tip of the second distal barb is greater than a second distance between an inner tip of the first proximal barb and an inner tip of the second proximal barb.

In one embodiment, the first leg tapers inwardly between the proximal and distal ends thereof, and the first leg has a cross-sectional area that is greater at the proximal end than at the distal end. In one embodiment, the second leg tapers inwardly between the proximal and distal ends thereof, and the second leg has a cross-sectional area that is greater at the proximal end than at the distal end.

In one embodiment, the first and second distal barbs extend inwardly toward one another and are aligned with one another along the respective longitudinal axes of the first and second legs, and the first and second proximal barbs extend inwardly toward one another and are aligned with one another along the respective longitudinal axes of the first and second legs.

In one embodiment, the distal end of the first leg includes a first insertion tip having a first distal piercing point, and the distal end of the second leg includes a second insertion tip having a second distal piercing point. The first and second insertion tips are desirably asymmetrical relative to the respective longitudinal axes of the first and second legs. In one embodiment, the first leg has a first outer wall that extends from a first end of the bridge to the first distal piercing point, and the second leg has a second outer wall that extends from a second end of the bridge to the second distal piercing point. In one embodiment, the distance between the first and second outer walls defines a width of the surgical fastener that remains constant between the first and second ends of the bridge and the first and second distal piercing points.

In one embodiment, the bridge includes a major surface that faces away from the distal ends of the first and second legs, and a crown that extends proximally from the major surface of the bridge. In one embodiment, the crown has a cruciform shape including a center section that is centered on the major surface of the bridge and first and second flanges that extend laterally from opposite sides of the center section. In one embodiment, the major surface of the bridge includes a first C-shaped section that surrounds the first flange, and a second C-shaped section that opposes the first section and that surrounds the second flange.

In one embodiment, a system for dispensing a surgical fastener includes an insertion tool having a distal end with a distal face and first and second C-shaped projections on opposite ends of the distal face that oppose one another and that extend distally from the distal face. In one embodiment, during insertion of a surgical fastener, the first C-shaped projection engages the first C-shaped section of the major face that surrounds the first flange of the crown, and the second C-shaped projection engages the second C-shaped section of the major face that surrounds the second flange of the crown for applying an insertion force to the proximal end of the surgical fastener.

In one embodiment, a proximal end of a surgical fastener includes a cruciform shaped crown that extends proximally from a bridge and a distal end of the insertion tool has a distal end with a negative cruciform shape that engages the cruciform shaped crown. The positive cruciform shape of the crown and the negative cruciform shape of the insertion tool enables the insertion tool to better control the orientation of the surgical fastener relative to the insertion tool and prevents twisting of the surgical fastener relative to the insertion tool.

In one embodiment, a surgical fastener is designed to minimize tissue bleeding associated with its use as a tissue fastener while not compromising functionality of the surgical fastener when used, for example, in the fixation of surgical mesh in ventral hernia repair procedures or in the fixation of tissue to tissue (e.g., peritoneum to fascia).

In one embodiment, a surgical fastener includes a crown having a top surface, a bottom surface, a first end, and a second end, a width and a length, a first prong extending from the first end, and a second prong extending from the second end. In one embodiment, each of the first and second prongs has a proximal end and a distal end, a barb integral with and extending from the distal end, a cross-sectional area of the proximal end, and a cross-sectional area of the distal end that is less than that of the proximal end.

In one embodiment, the cross-sectional area of the distal end of the prong transitions to that of the proximal end of the prong. In one embodiment, the prong transitions in a taper like fashion.

In one embodiment, the crown defines the greatest width of the surgical fastener and the proximal ends of the prongs do not extend beyond the width of the crown, which allows feeding of the fastener through a delivery device.

In one embodiment, the barbs extend inwardly from the distal ends of the prongs.

In one embodiment, the barb has a thickness that is less than that of the body of the prong.

In one embodiment, the outside (i.e., lateral) dimension between each prong is essentially the same as the length of the crown, which allows for feeding of the fastener through a delivery device.

These and other preferred embodiments of the present invention will be described in more detail below.

BRIEF DESCRIPTION OF THE DRAWING

FIGS. 5D-1 and 5D-2 show a method of guiding a surgical fastener and an insertion tool through an elongated channel of an applicator instrument, in accordance with one embodiment.

DETAILED DESCRIPTION OF PREFERRED EMBODIMENTS

Figure 1A:
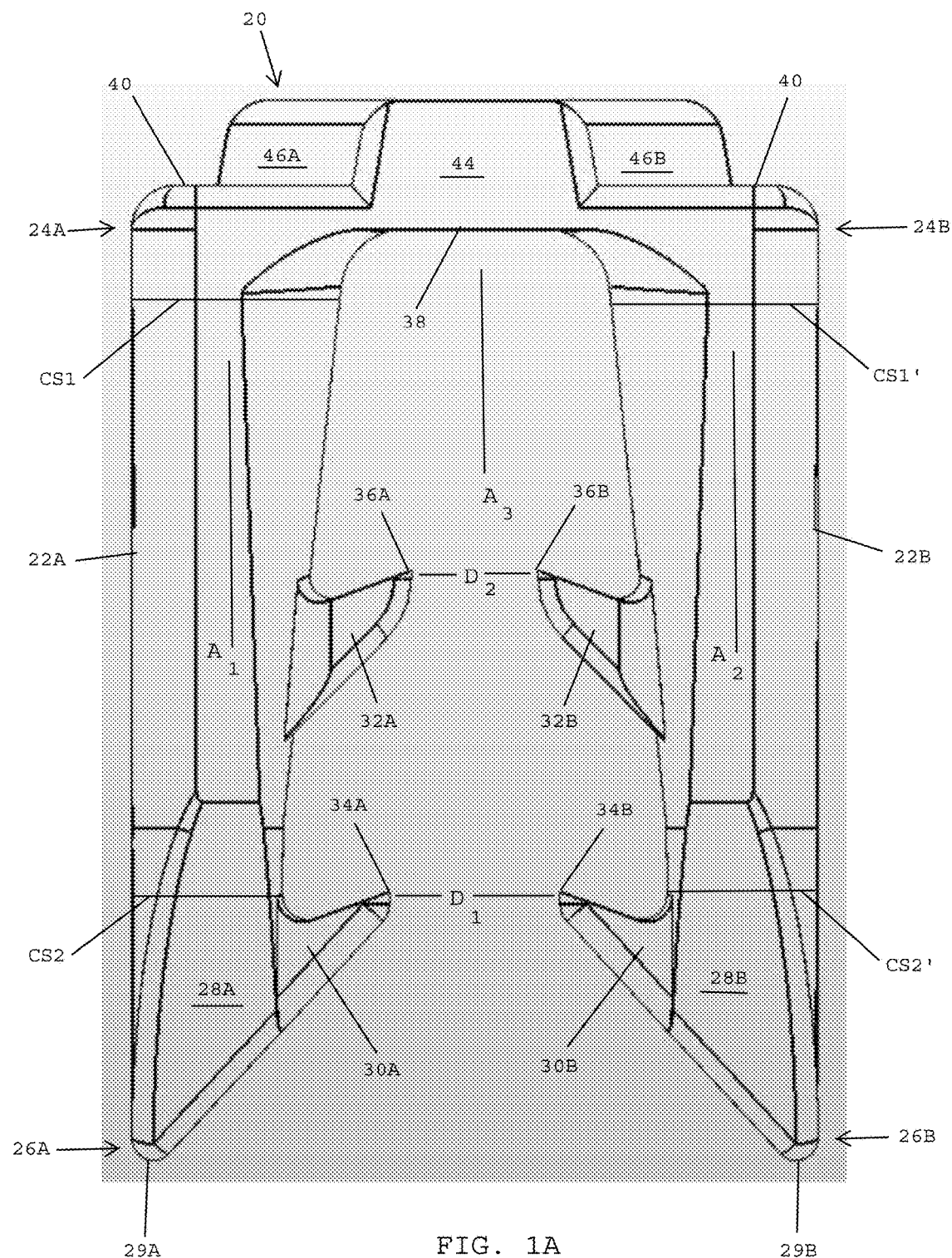
FIGS. 1A-1H show a surgical fastener used to secure prosthetic devices to tissue, in accordance with one embodiment.
Figure 1B:
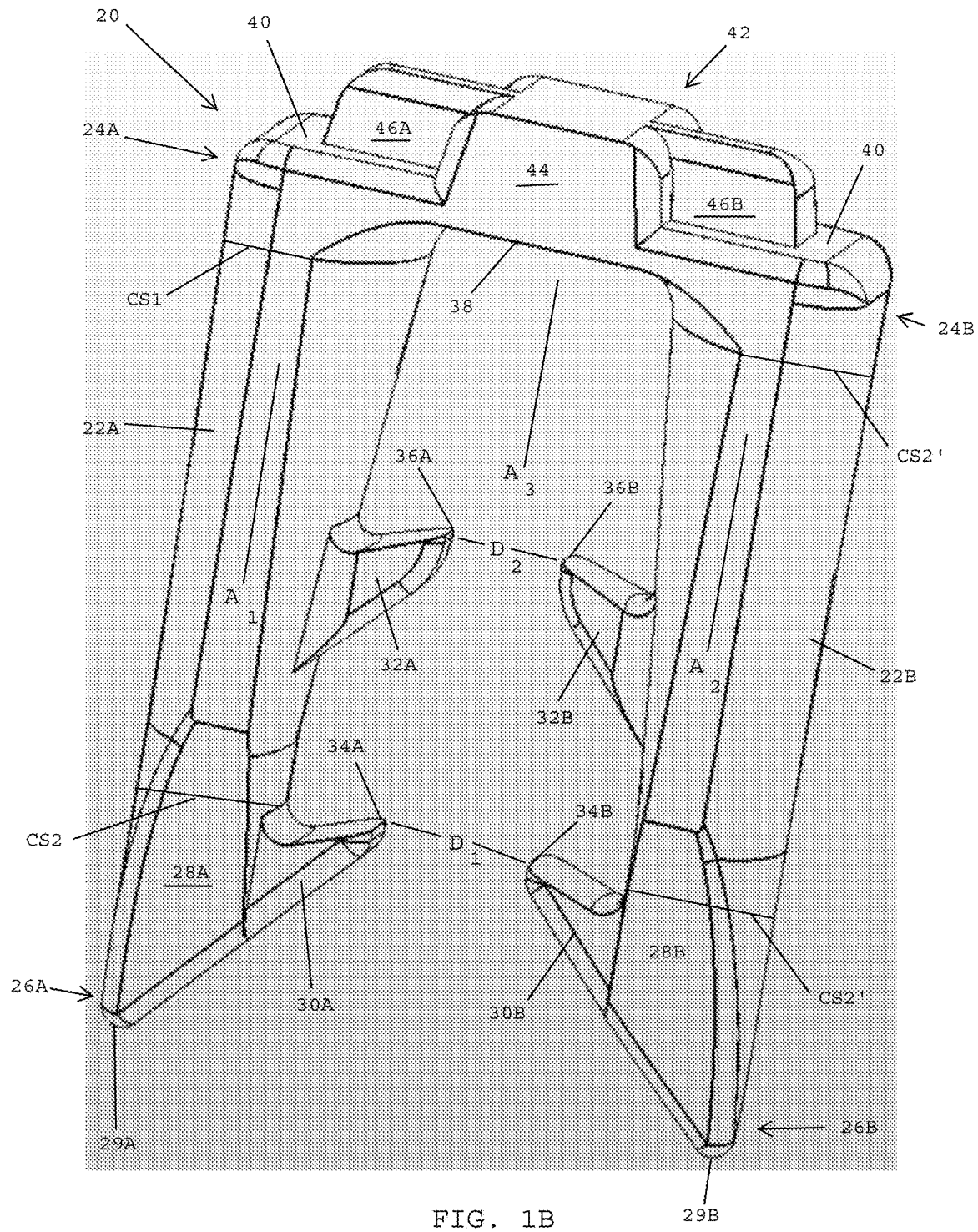
Figure 1C:
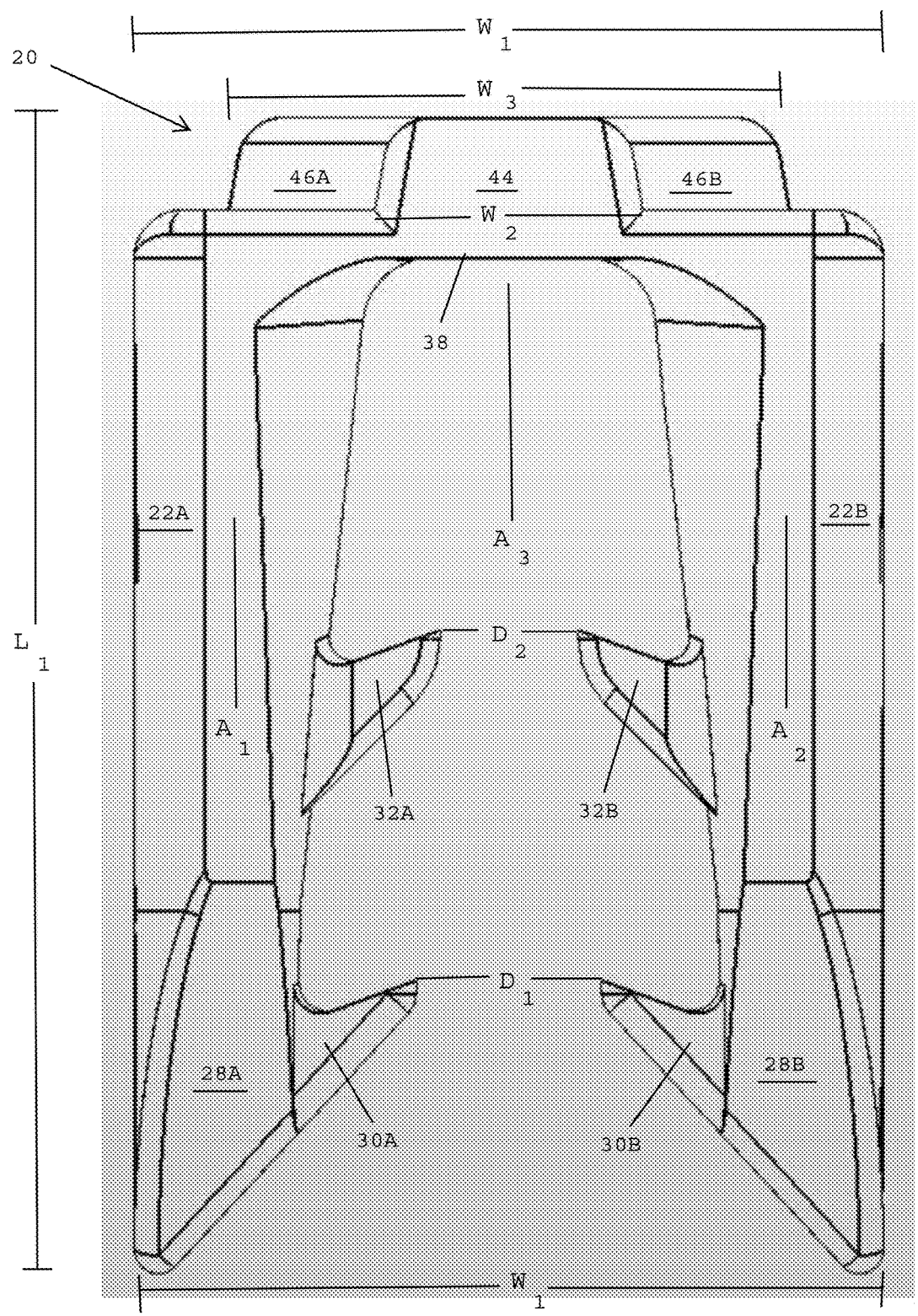

Referring to FIGS. 1A-1C, in one embodiment, a surgical fastener 20 for securing prosthetic devices to tissue preferably includes a first leg 22A having a proximal end 24A and a distal end 26A. In one embodiment, a first cross sectional area CS1 adjacent the proximal end 24A of the first leg 22A is greater than a second cross sectional area CS2 adjacent the distal end 26A of the first leg 22A. In one embodiment, the first leg 22A tapers inwardly between the proximal end 24A of the first leg 22A and the distal end 26A of the first leg 22A. In one embodiment, the largest cross sectional area of the first leg is adjacent the proximal end 24A of the first leg and the first leg tapers inwardly between the proximal end and the distal end thereof.

In one embodiment, the first leg 22A extends along a first longitudinal axis $A_1$. In one embodiment, the first leg 22A includes an insertion tip 28A located at the distal end 26A of the first leg. In one embodiment, the insertion tip 28A has a distal-most point 29A. In one embodiment, the insertion tip 28A is asymmetrical so that it skews outwardly relative to the longitudinal axis $A_1$ of the first leg 22A.

In one embodiment, the surgical fastener 20 preferably includes a second leg 22B having a proximal end 24B and distal end 26B. The second leg 22B desirably has a first cross sectional area CS1' adjacent the proximal end 24B that is greater than a second cross sectional CS2' adjacent the distal end 26B. In one embodiment, the second leg 22B tapers inwardly between the proximal end 24B of the second leg 22B and the distal end 26B of the second leg 22B. In one embodiment, the second leg 22B has an insertion tip 28B located at the distal end thereof. In one embodiment, the insertion tip 28B has a distal-most point 29B. In one embodiment, the second leg 22B extends along a second longitudinal axis $A_2$ that is parallel to the first longitudinal axis $A_1$ of the first leg 22A. In one embodiment, the insertion tip 28B on the second leg 22B is asymmetrical and skews outwardly relative to the second longitudinal axis $A_2$ of the second leg 22B.

In one embodiment, the proximal ends of the respective first and second legs 22A, 22B have respective cross-sections that define convex surfaces or cylindrical shapes that are designed to plug the entrance holes created by the insertion tips of the legs entering tissue so as to prevent and/or reduce bleeding from the entrance holes.

In one embodiment, the first leg 22A includes a distal barb 30A. In one embodiment, the distal barb 30A is positioned adjacent the distal end 26A of the first leg 22A and is proximal to the distal-most point 29A on the insertion tip 28A. The distal barb 30A preferably extends inwardly toward the second leg 22B. In one embodiment, the first leg 22A has a proximal barb 32A that also extends inwardly toward the second leg 22B. In one embodiment, the proximal barb 32A on the first leg 22A is located between the proximal end 24A of the first leg 22A and the distal barb 30A. In one embodiment, the proximal barb 32A is located about halfway between the proximal end 24A and the distal end 26A of the first leg 22A.

In one embodiment, the second leg 22B of the surgical fastener 20 preferably includes a distal barb 30B that extends inwardly toward the first leg 22A. In one embodiment, the distal barbs 30A, 30B on the respective first and second legs 22A, 22B oppose one another, extend toward one another, and are aligned with one another along the lengths of the respective first and second legs 22A, 22B.

In one embodiment, the second leg 22B includes a proximal barb 32B that extends inwardly toward the first leg 22A. In one embodiment, the proximal barbs 32A, 32B on the respective first and second legs 22A, 22B extend toward one another, oppose one another, and are aligned with one another along the lengths of the respective first and second legs 22A, 22B.

In one embodiment, the surgical fastener 20 extends along a central axis $A_3$ that bisects the surgical fastener 20 into a first half including the first leg 22A with the associated barbs 30A, 32A, and a second half including the second leg 22B with the associated barbs 30B, 32B. The central axis $A_3$ is preferably parallel to both the first longitudinal axis $A_1$ of the first leg 22A and the second longitudinal axis $A_2$ of the second leg 22B. In one embodiment, the central axis $A_3$ bisects the surgical fastener 20 for splitting the surgical fastener into two evenly sized parts and is equidistant from the first longitudinal axis $A_1$ of the first leg 22A and the second longitudinal axis $A_2$ of the second leg 22B.

In one embodiment, the distal barb 30A on the first leg 22A has an inner tip 34A and the distal barb 30B on the second leg 22B has an inner tip 34B. The respective inner tips 34A, 34B define a distance $D_1$ that extends along an axis that is perpendicular to the central axis $A_3$ of the surgical fastener 20.

In one embodiment, the proximal barb 32A on the first leg 22A has an inner tip 36A and the proximal barb 32B on the second leg 22B has an inner tip 36B. The inner tips 36A, 36B define a distance $D_2$ that extends along an axis that is perpendicular to the central axis $A_3$ of the surgical fastener 20. In one embodiment, the distance $D_1$ between the inner tips 34A, 34B of the respective distal barbs 30A, 30B is greater than the distance $D_2$ between the inner tips 36A, 36B of the proximal barbs 32A, 32B. In one embodiment, the distance $D_1$ is about 0.040 inches and the distance $D_2$ is about 0.030 inches.

In one embodiment, the first and second insertion tips 28A, 28B are advanced into tissue followed by the first and second distal barbs 30A, 30B to form two spaced tissue openings. In one embodiment, the two tissue openings will be about 0.040 inches apart from one another, which is equal to the distance $D_1$ between the inner tips 34A, 34B of the first and second distal barbs 30A, 30B. In one embodiment, the first and second proximal barbs 32A, 32B are closer together than are the first and second distal barbs 30A, 30B, which enables the first and second proximal barbs 32A, 32B to grip onto the side walls of the tissue openings previously formed by the first and second distal barbs 30A, 30B. Thus, an important tissue anchoring benefit is gained by providing proximal barbs 32A, 32B that are closer together than the distal barbs 30A, 30B.

In one embodiment, the surgical fastener 20 may be made of absorbable and/or non-absorbable materials. Preferred absorbable materials include PDS, PDS/lactide-glycolide blends, PLA, etc. In one embodiment, each surgical fastener is sized to fit inside of a 5 mm outer diameter tube (typically trocar cannula dimension). The surgical fastener is fabricated by molding, however, with small modifications, other processes such as casting, stamping, and machining may be used. In one embodiment, the surgical fasteners may be extruded into a general shape, and then formed. In one embodiment, the surgical fasteners may be printed using a 3-D printer.

Referring to FIGS. 1A-1D, in one embodiment, the surgical fastener 20 preferably includes a bridge 38 that interconnects the proximal ends 24A, 24B of the respective first and second legs 22A, 22B. The central axis $A_3$ of the surgical fastener 20 desirably bisects the bridge. In one embodiment, the bridge 38 includes a major surface 40 that extends adjacent the proximal ends 24A, 24B of the first and second legs 22A, 22B, and a crown 42 that projects proximally from the major surface 40 to define a proximal-most portion of the surgical fastener 20. In one embodiment, the major surface 40 is flat. As will be described in more detail herein, the crown 42 is preferably engaged by a leading end of a firing rod or by an insertion tool secured to the leading end of a firing rod for applying an insertion force to the surgical fastener and controlling the orientation of the surgical fastener as the surgical fastener is dispensed from an applicator instrument. In one embodiment, the crown 42 includes a center section 44 that spans the thickness $T_1$ (FIG. 1D) of the surgical fastener 20 and first and second lateral flanges 46A, 46B that extend laterally from the center section 44.

Figure 1D:
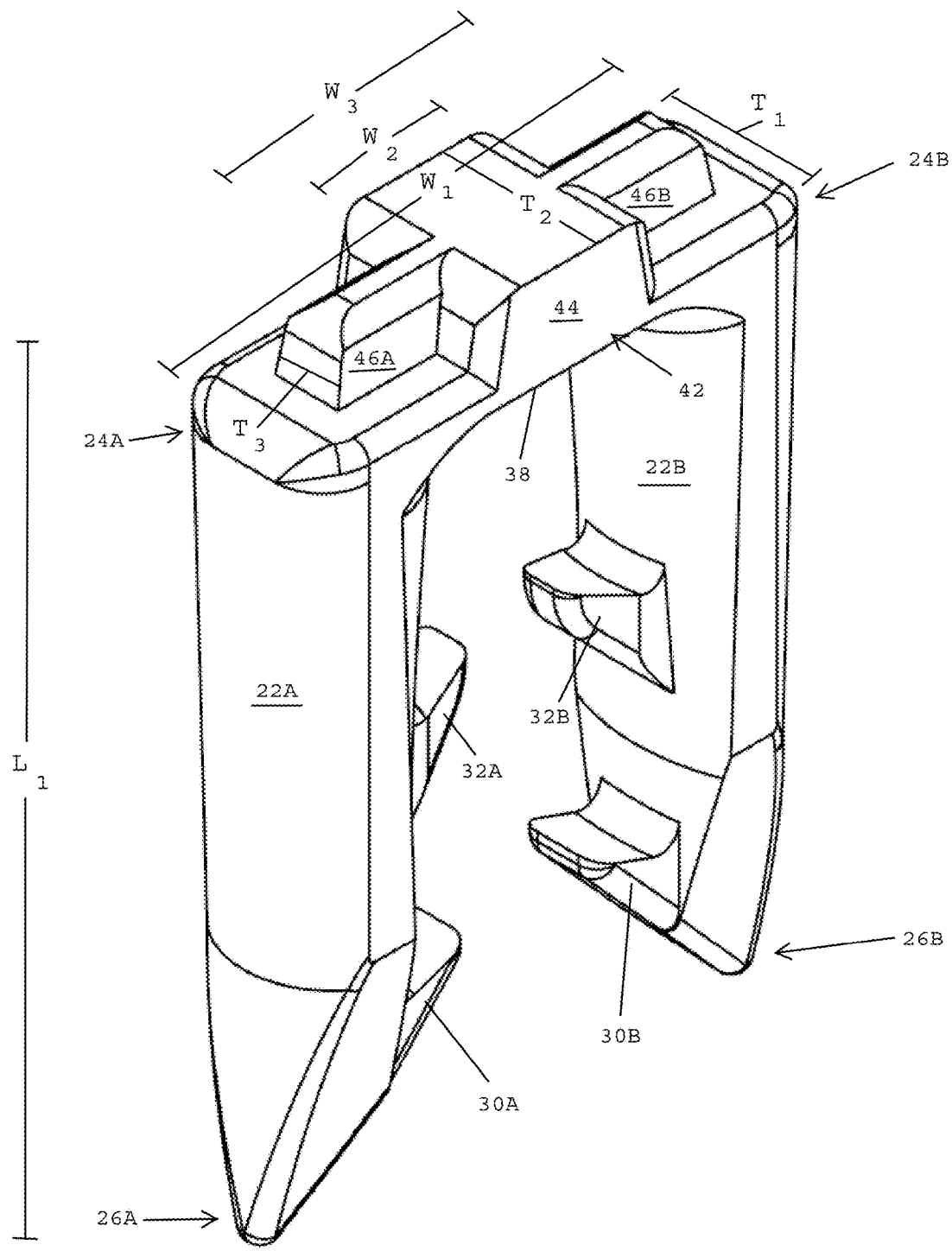

Referring to FIGS. 1C and 1D, in one embodiment, the surgical fastener 20 has a length $L_1$ of about 0.248 inches, a width $W_1$ of about 0.160 inches, and a thickness $T_1$ of about 0.050 inches. In one embodiment, the width $W_1$ of the surgical fastener 20 is the same at both the proximal and distal ends thereof, and the width $W_1$ remains constant between the proximal and distal ends of the surgical fastener. In other words, the width $W_1$ defined by the distance between the outer surfaces of the first and second legs 22A, 22B at the proximal ends 24A, 24B of the legs equals the distance between the outer surfaces of the insertion tips 28A, 28B at the distal ends of the first and second legs 22A, 22B. In one embodiment, the cross-sectional areas of the legs decrease between the proximal and distal ends of the respective first and second legs 22A, 22B, however, the width $W_1$ of the surgical fastener remains constant between the proximal and distal ends of the first and second legs.

In one embodiment, the center section 44 of the crown 42 has a width $W_2$ of about 0.057 inches and the laterally extending flanges 46A, 46B define a width $W_3$ of about 0.120 inches.

Figure 1E:
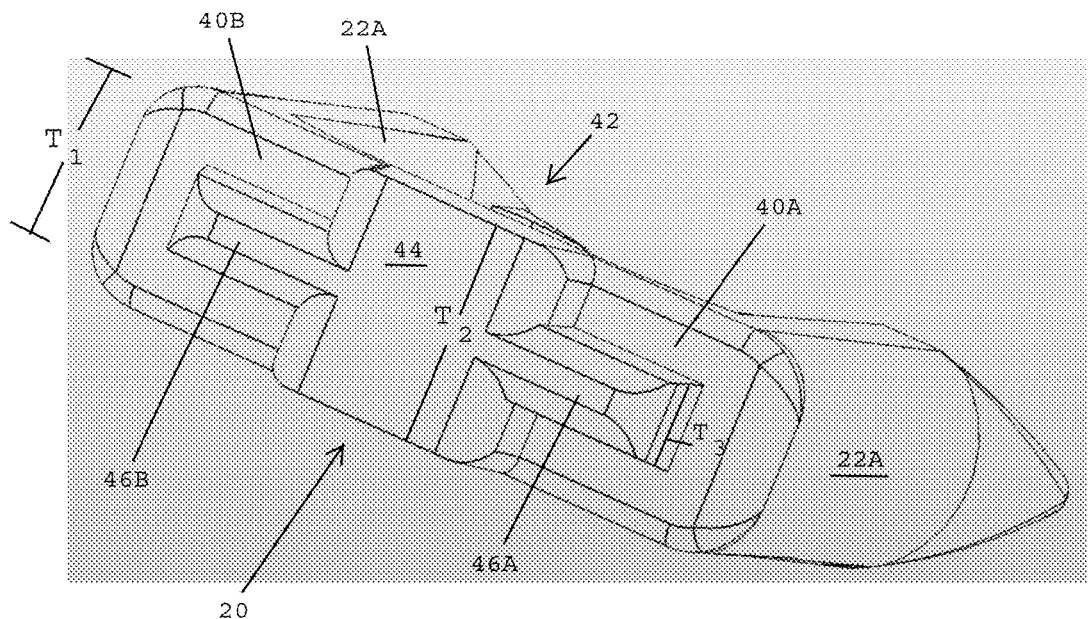

Referring to FIGS. 1D and 1E, the center section 44 of the crown 42 defines a thickness $T_2$ that equals the thickness $T_1$ of the surgical fastener 20. In one embodiment, the laterally extending flanges 46A, 46B have a thickness $T_3$ of about 0.020 inches.

Figure 1F:
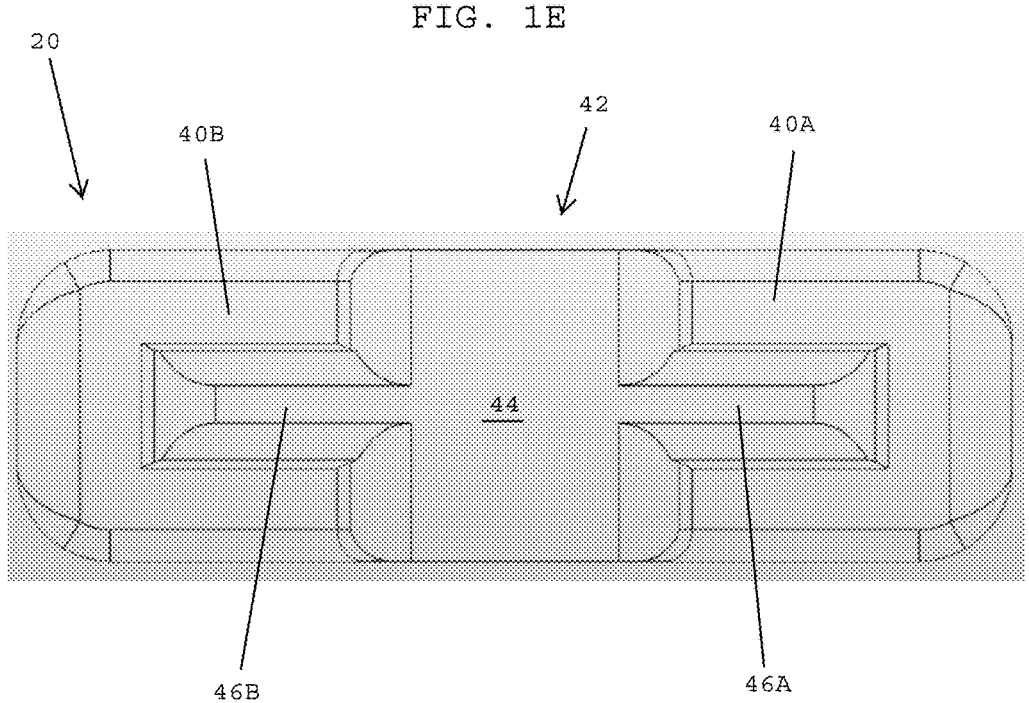

Referring to FIGS. 1E and 1F, in one embodiment, the crown 42 at the proximal end of the surgical fastener 20 desirably includes the center section 44 and the first and second laterally extending flanges 46A, 46B that extend laterally from the center section 44. The major surface 40 of the bridge extends around the sides of the respective first and second laterally extending flanges 46A, 46B. In one embodiment, a first section 40A of the major surface 40 extends around the first laterally extending flange 46A and has a C-shape, and a second section 40B of the major surface 40 extends around the second laterally extending flange 46B and has a C-shape. The C-shaped first and second sections 40A, 40B of the major surface 40 have the same shape and configuration and oppose one another on opposite sides of the center section 44. In one embodiment, the C-shaped sections 40A, 40B are aligned with the respective longitudinal axes $A_1$, $A_2$ of the first and second legs 22A, 22B (FIG. 1A).

Figure 1G:
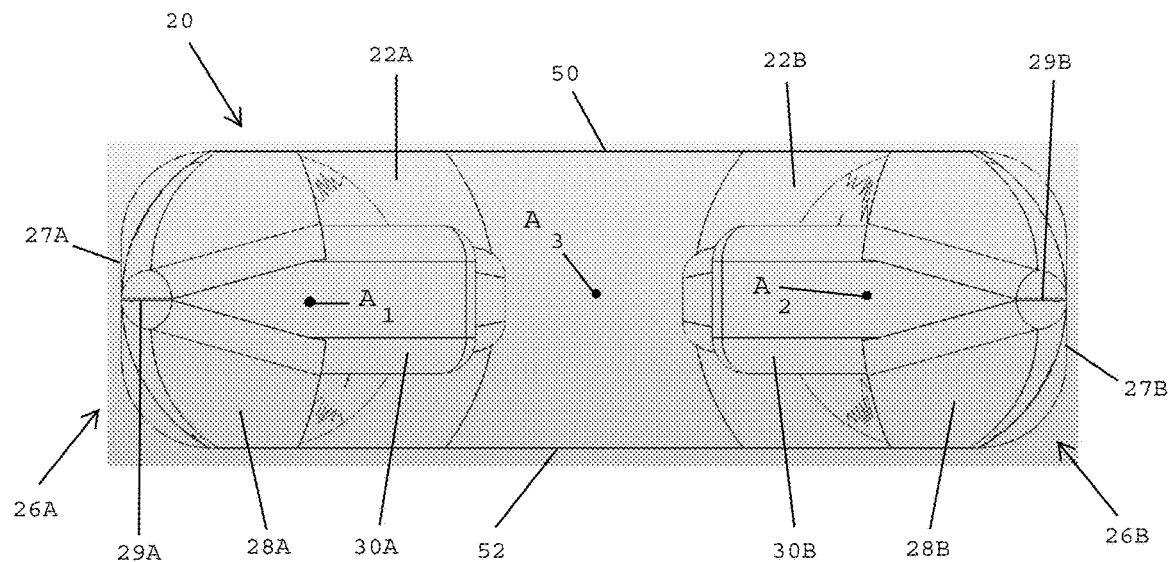

Referring to FIG. 1G, in one embodiment, the first leg 22A of the surgical fastener 20 has a distal end 26A with the first insertion tip 28A having the distal-most point 29A. In one embodiment, the first insertion tip 28A is skewed outwardly relative to the longitudinal axis $A_1$ of the first leg 22A. The first leg 22A includes the distal barb 30A that extends inwardly toward the second leg 22B of the surgical fastener 20. The second leg 22B has a distal end 26B with the second insertion tip 28B having the distal-most point 29B. In one embodiment, the second insertion tip 28B is skewed outwardly relative to the longitudinal axis $A_2$ of the second leg 22B. The second leg 22B includes the distal barb 30B that extends inwardly toward the first leg 22A. In one embodiment, the distal barbs 30A, 30B extend toward one another, oppose one another, and are aligned with one another adjacent the distal ends 26A, 26B of the respective first and second legs 22A, 22B. The central axis $A_3$ bisects the surgical fastener into a first half including the first leg 22A and a second half including the second leg 22B.

Figure 1H:
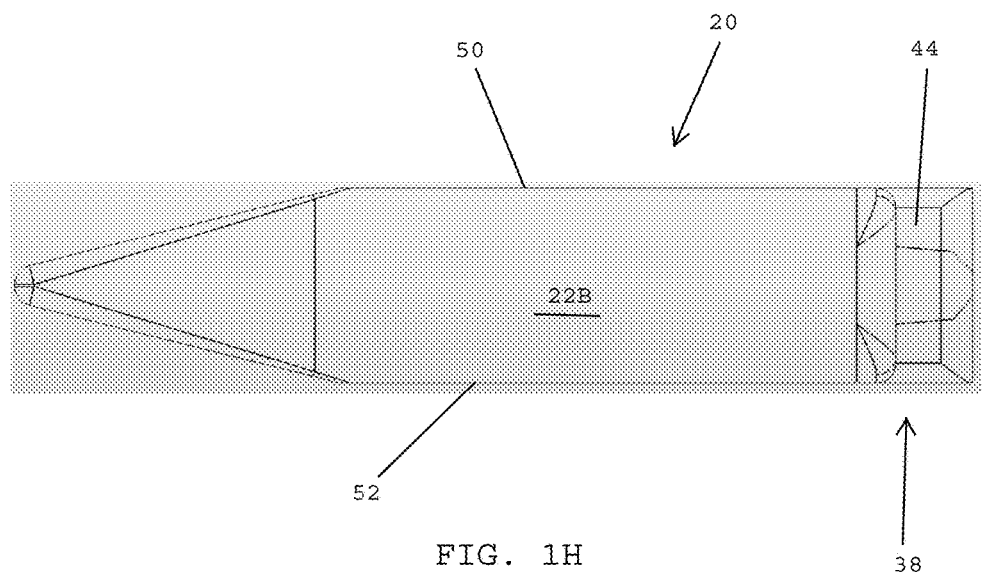

Referring to FIGS. 1D and 1G, in one embodiment, the first distal barb 30A and the first proximal barb 32A have respective thicknesses that are less than the thickness or diameter of the first leg 22A, and the second distal barb 30B and the second proximal barb 32B have respective thicknesses that are less than the thickness or diameter of the second leg 22B Referring to FIGS. 1G and 1H, in one embodiment, the surgical fastener 20 desirably includes a first major surface 50 that extends over a top side of the surgical fastener 20 and a second major surface 52 that extends over an underside of the surgical fastener 20. In one embodiment, the first major surface 50 is flat and extends over the center section 44 of the crown 42 and the first and second legs 22A, 22B of the surgical fastener. In one embodiment, the second major surface 52 is also flat and extends over opposite sides of the center section 44 of the crown 42 and the first and second legs 22A, 22B. The flat, first and second major surfaces 50, 52 may be used to control the orientation of the surgical fastener as it moves distally through the shaft of an applicator instrument.

In one embodiment, the first leg 22A desirably has an outer surface 27A that extends along the length of the first leg. In one embodiment, the outer surface 27A of the first leg 22A may include a flat surface that is used to control the orientation of the surgical fastener as it moves distally through the shaft of an applicator instrument. In one embodiment, the second leg 22B desirably has an outer surface 27B that extends along the length of the second leg. In one embodiment, the outer surface 27B of the second leg 22B may include a flat surface that is used to control the orientation of the surgical fastener as it moves distally thorough the shaft of an applicator instrument.

Figure 2:
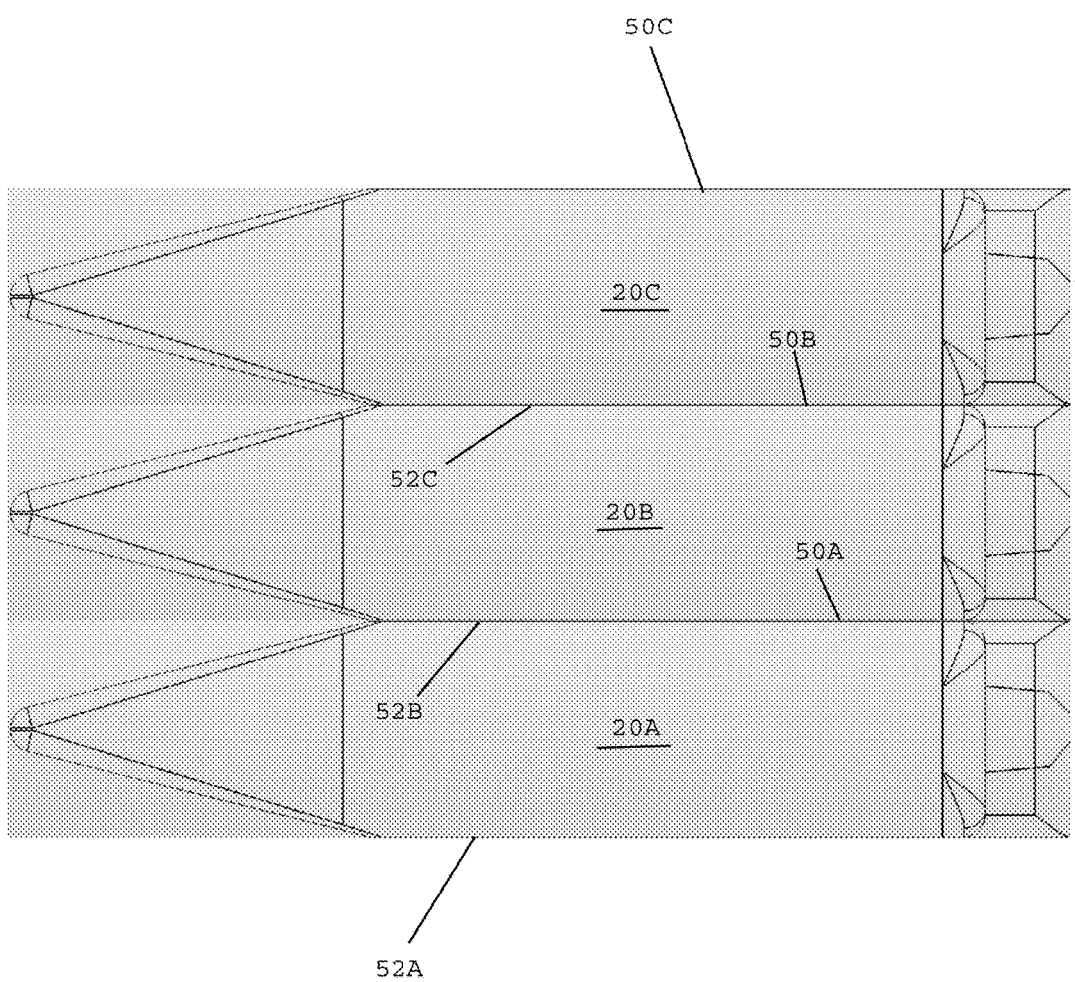
FIG. 2 shows the surgical fastener of FIGS. 1A-1H in a stacked array, in accordance with one embodiment.

Referring to FIGS. 1H and 2, in one embodiment, the flat top and bottom major surfaces 50, 52 of the surgical fastener 20 enable a plurality of surgical fasteners to be stacked one atop another with the flat major surfaces of adjacent surgical fasteners engaging one another within the stack. FIG. 2 shows a stack of three surgical fasteners 20A-20C. The bottom surgical fastener 20A in the stack has a flat top surface 50A and a flat bottom surface 52A. The flat bottom surface 52B of the second surgical fastener 20B in the stack is in contact with the flat top surface 50A of the first surgical fastener 20A. The flat bottom surface 52C of the third surgical fastener 20C in the stack is in contact with the flat top surface 50B of the second surgical fastener 20C. As shown in FIG. 2, the flat major surfaces of the respective surgical fasteners are in contact with one another for maintaining the respective surgical fasteners in the stacked array. Although FIG. 2 shows three stacked surgical fasteners 20A-20C, in other embodiments, the number of surgical fasteners in a stack may be five, 10, 20, 30, or more. In one embodiment, the surgical fasteners may be loaded into a cartridge to form a stack of deployable surgical fasteners.

Referring to FIGS. 3A-3D, in one embodiment, an insertion tool 60 is used for advancing surgical fasteners toward a distal end of an applicator instrument. In one embodiment, the insertion tool 60 preferably includes a proximal end 62 that may be coupled with a distal end of a firing rod and a distal end 64 that is adapted to engage the proximal end of a surgical fastener.

Referring to FIGS. 1A, 1E, and 3A-3D, in one embodiment, the insertion tool 60 preferably includes opposing C-shaped projections 66A, 66B that oppose one another at the distal most end of the insertion tool. In one embodiment, the C-shaped projections are designed to engage the C-shaped surfaces 40A, 40B of the bridge at the proximal end of the surgical fastener 20. In one embodiment, the insertion tool 60 includes a distal surface 68, such as a flat surface, adjacent the distal end of the insertion tool that is surrounded by the opposing C-shaped projections 66A, 66B. In one embodiment, the crown 42 at the proximal end of the surgical fastener is disposed within the space bounded by the C-shaped projections 66A, 66B. The distal surface 68 may engage the center section 44 and the first and second laterally extending flanges 46A, 46B of the crown at the proximal end of a surgical fastener. In one embodiment, the center section 44 and laterally extending flanges 46A, 46B of the insertion control surface 42 has a height $H_1$ (FIG. 1C) and the C-shaped projections 66A, 66B have a height $H_2$ (measured from surface 68) that is greater than the height $H_1$ so that the distal surface 68 is spaced from the crown 42 when the C-shaped projections 66A, 66B engage the flat surfaces 40A, 40B. As a result, all of the insertion force transferred from the insertion tool 60 to the surgical fastener 20 is transferred via the C-shaped projections 66A, 66B of the insertion tool engaging the C-shaped surfaces 40A, 40B aligned with the proximal ends of the respective first and second legs 22A, 22B.

In one embodiment, the insertion tool 60 preferably includes a stripper ramp 70 that extends above the C-shaped projections 66A, 66B at the distal end thereof. The stripper ramp 70 has a distal face 72 that lies in a plane with the distal faces 74 of the respective C-shaped projections 66A, 66B. In one embodiment, the insertion tool includes an attachment flange 75 at the proximal end 62 thereof that is coupled with the distal end of a firing rod so that the insertion tool may move distally and proximally with the firing rod.

In one embodiment, the insertion tool 60, coupled with the distal end of a firing rod via the attachment flange 75, is advanced distally toward the proximal end of a surgical fastener whereupon the distal-most face 72 of the ramp 70 engages the crown 42 (FIG. 1) at the proximal end of the surgical fastener. As the insertion tool advances distally, the proximal end of the surgical fastener is desirably directed into alignment with the major distal surface 68 at the distal end 64 of the insertion tool 60 so that the center section 44 and the first and second laterally extending flanges 46A, 46B (FIG. 1E) of the crown 42 are disposed between the opposing C-shaped projections 66A, 66B.

Referring to FIGS. 3A-3D, in one embodiment, the insertion tool 60 has a flat top surface 90, a flat bottom surface 92, a first flat side surface 94A, and a second flat side surface 94B. As will be described in more detail herein, in one embodiment, the flat surfaces 90, 92, 94A, and 94B are used to control the orientation of the insertion tool 60 as it moves distally in an applicator instrument.

Figure 3A:
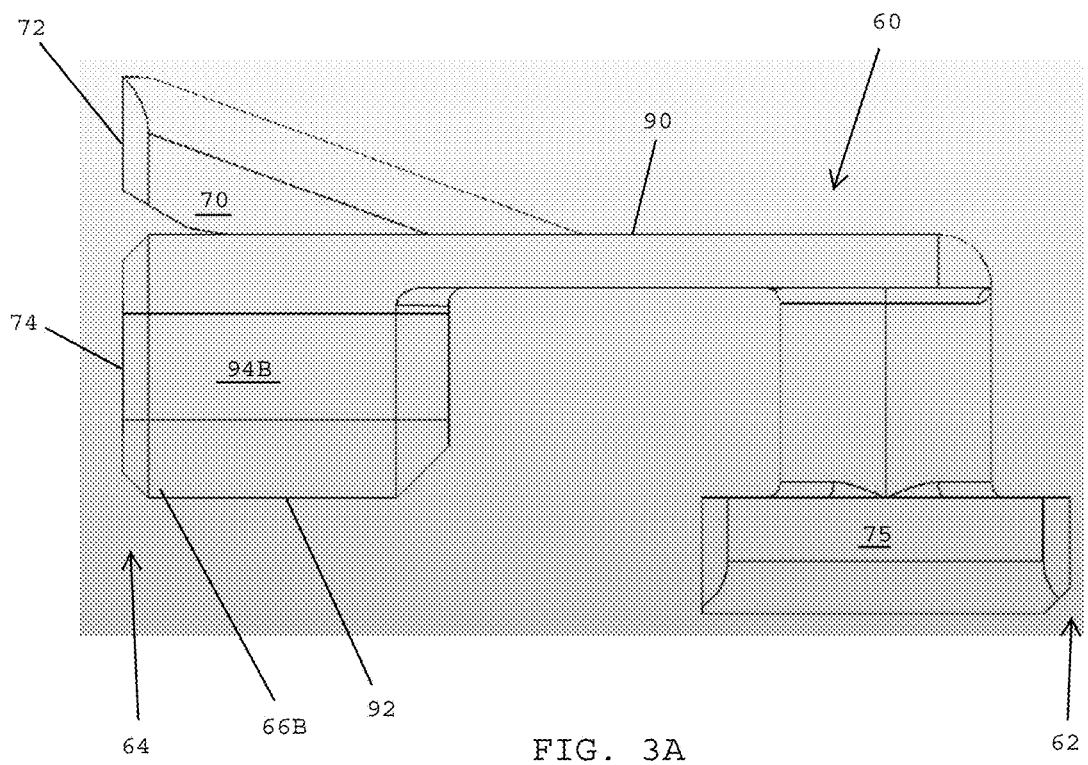
FIGS. 3A-3D show an insertion tool used to dispense the surgical fastener of FIGS. 1A-1H from an applicator instrument, in accordance with one embodiment.
Figure 3B:
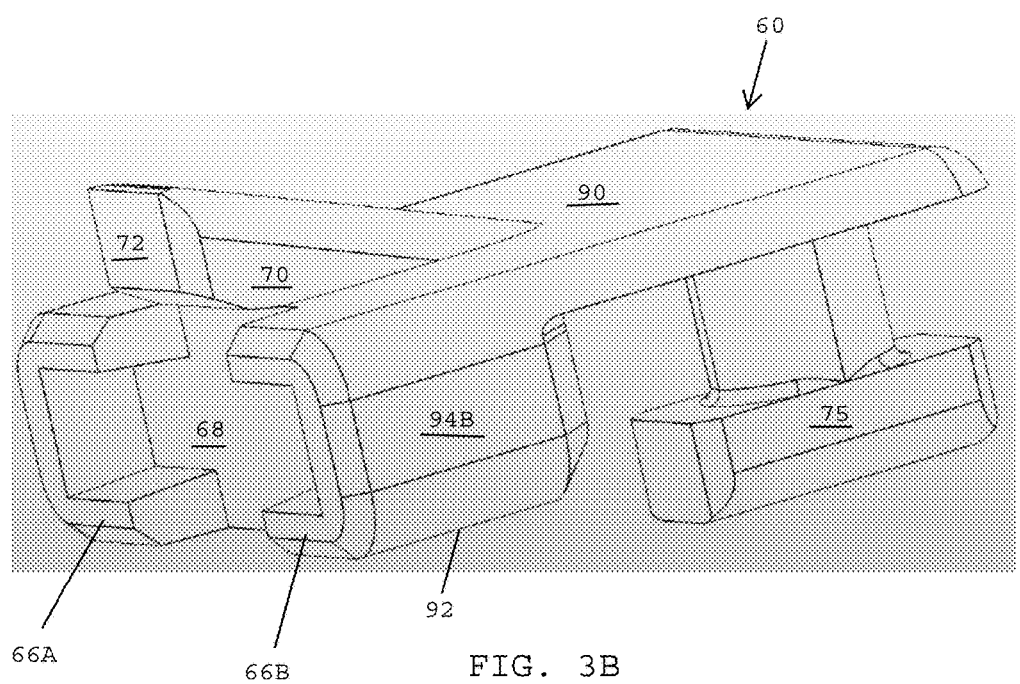
Figure 3C:
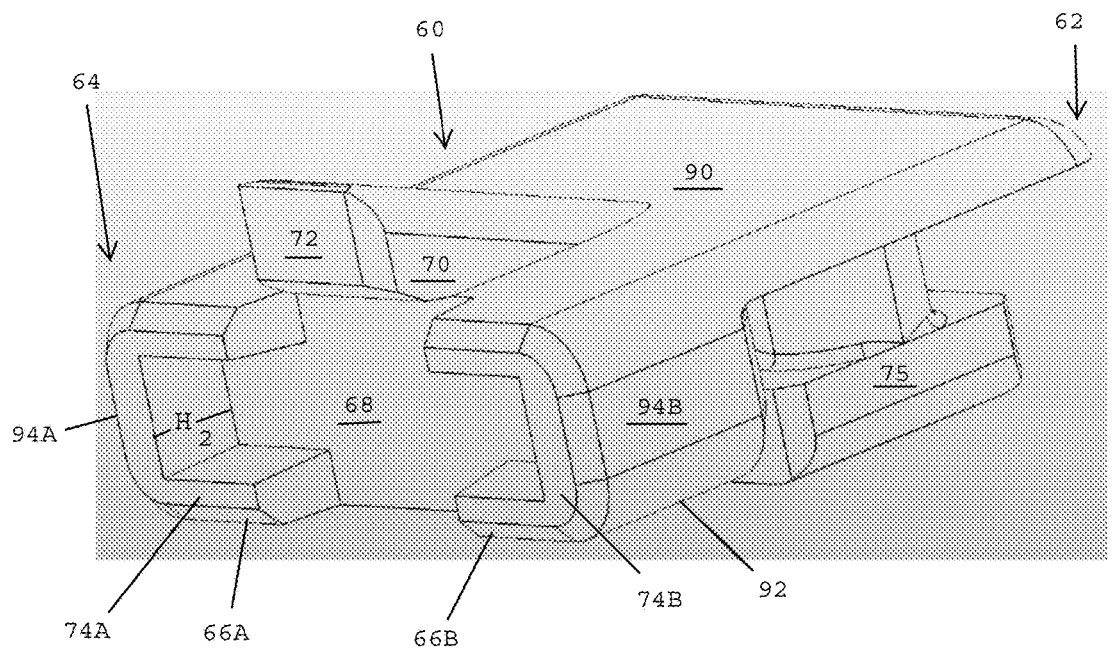
Figure 3D:
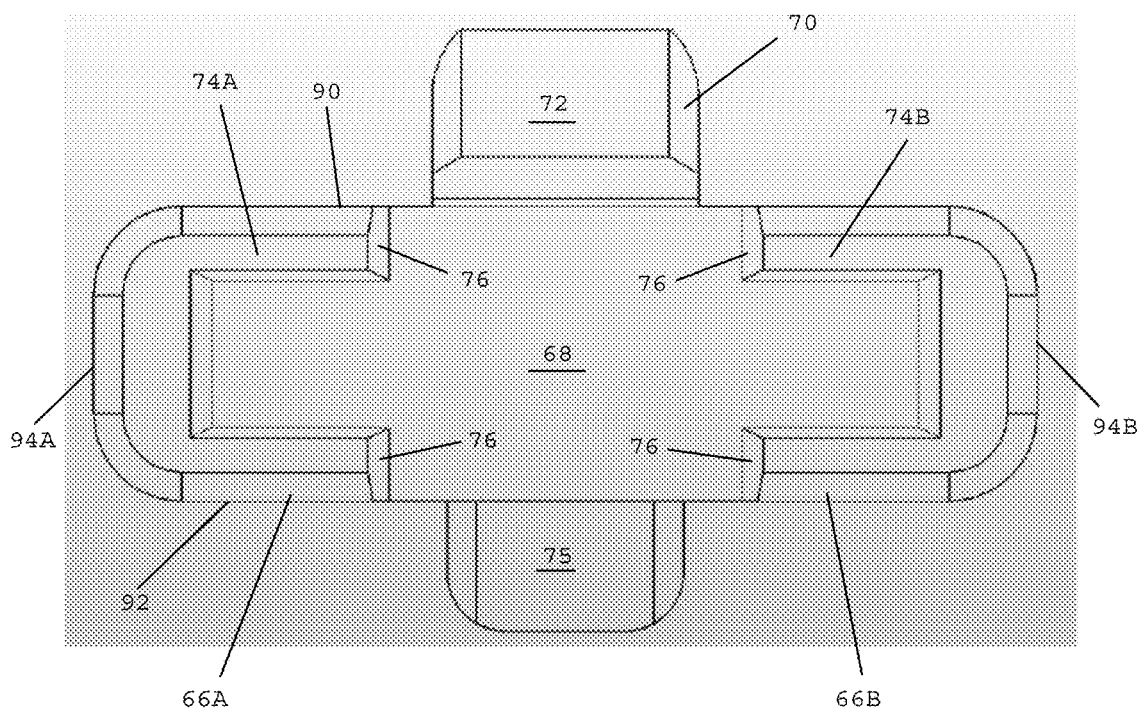
Figure 4A:
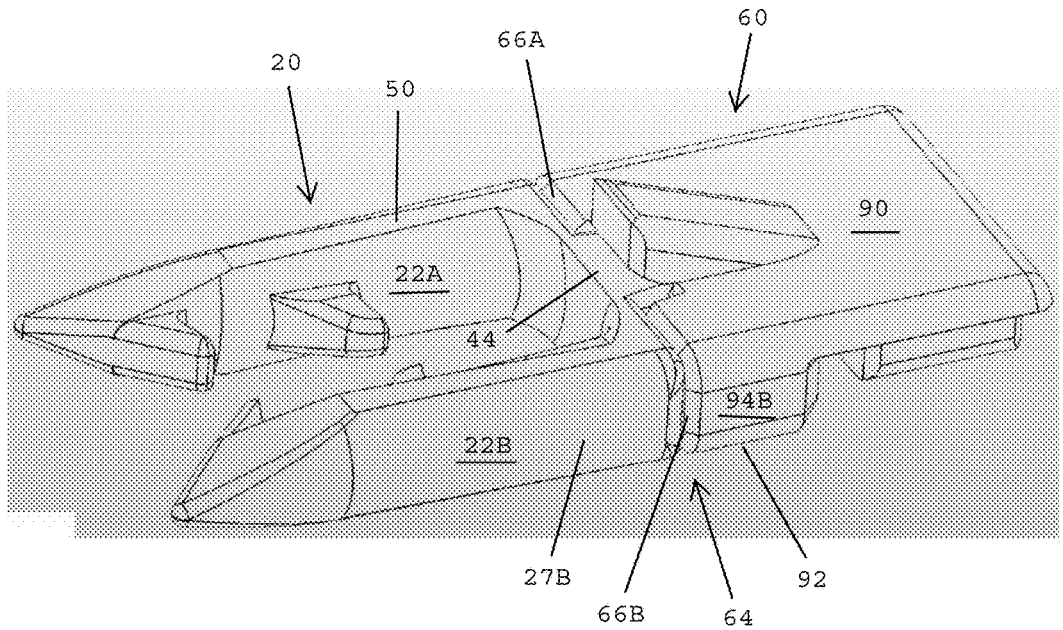
FIGS. 4A-4D show the insertion tool of FIGS. 3A-3D engaged with the surgical fastener of FIGS. 1A-1H.
Figure 4B:
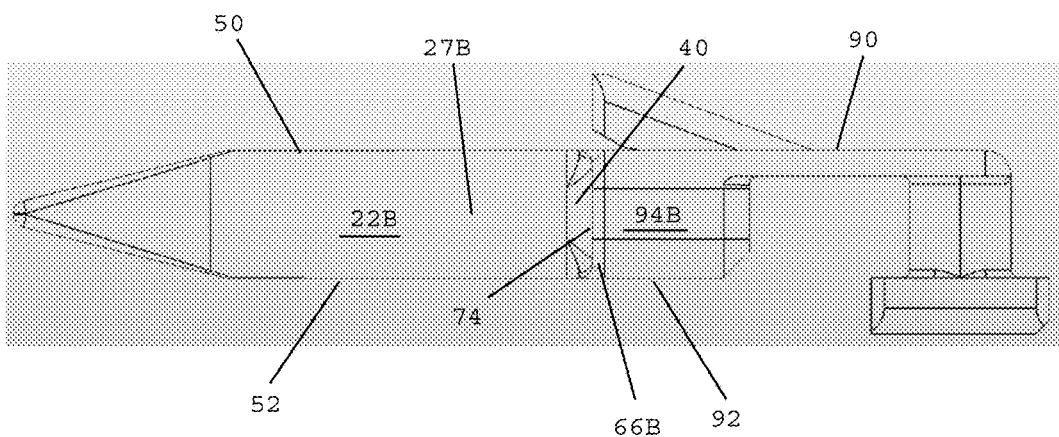
Figure 4C:
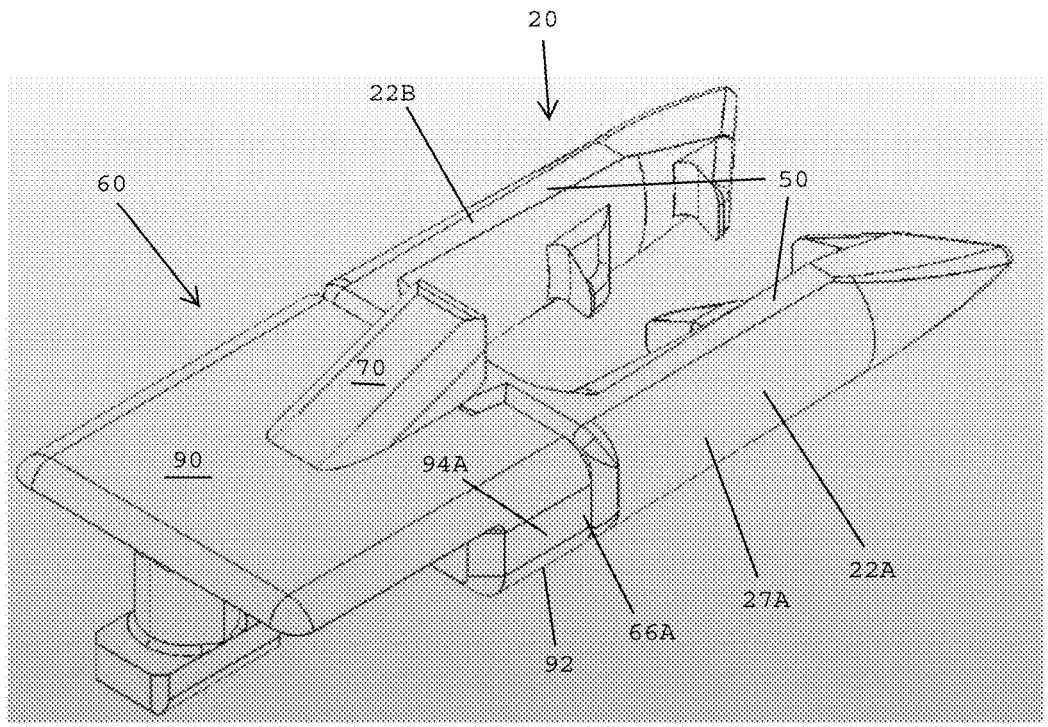
Figure 4D:
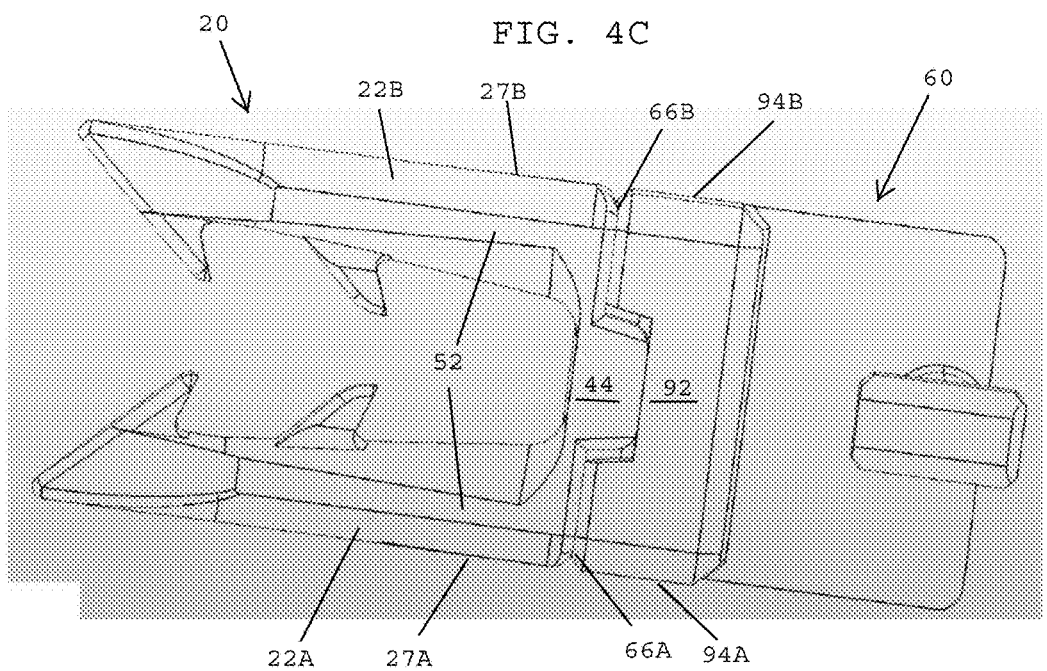

Referring to FIGS. 1E and 3D, in one embodiment, when the insertion tool engages the proximal end of the surgical fastener, the lateral side surfaces of the center section may engage the ends 76 of the opposing C-shaped projections 66A, 66B for further controlling the orientation of the surgical fastener as it is advanced distally by the insertion tool 60.

Referring to FIGS. 1D and 4A-4D, in one embodiment, the insertion tool 60 may be advanced until the distal end 64 of the insertion tool captures the crown 42 (FIG. 1A) located at the proximal end of the surgical fastener 20. In one embodiment, the center section 44 and the first and second laterally extending flanges 46A, 46B (FIG. 1A) of the crown 42 are captured between the first C-shaped projection 66A and the second C-shaped projection 66B at the distal end 64 of the insertion tool 60. The distal face 74 of the C-shaped projections 66A, 66B preferably abut against the C-shaped surfaces 40A, 40B (FIG. 1E) provided at the proximal ends of the respective first and second legs 22A, 22B. In one embodiment, the C-shaped projections 66A, 66B have a height $H_2$ (FIG. 3C) that is greater than 0.020 inches so that the major distal surface 68 of the insertion tool 60 does not engage the crown 42 at the proximal end of the surgical fastener. As a result, all of the insertion force that is transferred from the insertion tool 60 to the surgical fastener 20 is transmitted via the C-shaped projections 66A, 66B engaging the C-shaped surfaces 40A, 40B aligned with the proximal ends of the first and second legs 22A, 22B.

Referring to FIGS. 4A-4D, in one embodiment, when the crown of the surgical fastener 20 is engaged by the distal end of the insertion tool 60, the flat top surface 90 of the insertion tool 60 is aligned with the flat top surface 50 of the surgical fastener 20, the flat bottom surface 92 of the insertion tool 60 is aligned with the flat bottom surface 52 of the surgical fastener 20, the first flat side surface 94A of the insertion tool 60 is aligned with the flat side surface 27A of the first leg 22A of the surgical fastener 20, and the second flat side surface 94B of the insertion tool 60 is aligned with the flat side surface 27B of the second leg 22B of the surgical fastener 20.

Figure 5A:
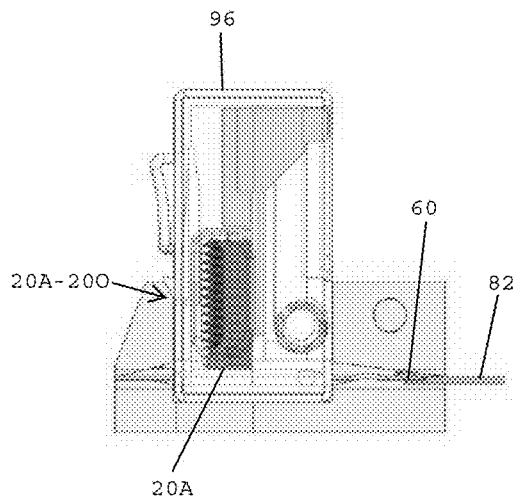
FIGS. 5A-5D show a stack surgical fasteners loaded into a magazine and a method stripping and dispensing a single surgical fastener from the bottom of the stack, in accordance with one embodiment.

Referring to FIG. 5A, in one embodiment, a plurality of surgical fasteners 20A-20O are stacked atop one another and loaded into a dispensing cartridge 96 that feeds the surgical fasteners to the firing system of an applicator instrument. A first surgical fastener 20A at the bottom of the stack is positioned within a channel for being engaged by the distal end of the insertion tool 60 (FIGS. 4A-4D). In one embodiment, the insertion tool 60 is secured to a distal end of a firing rod 82.

Figure 5B:
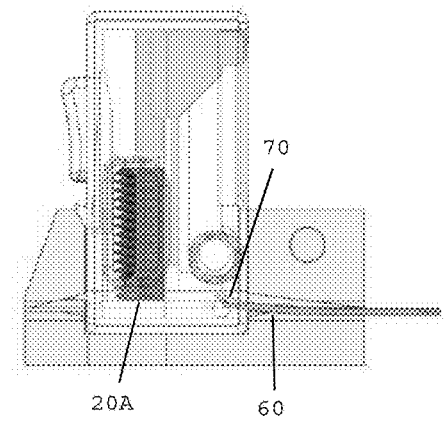

Referring to FIG. 5B, in one embodiment, the insertion tool 60 continues to advance distally toward the proximal end (i.e., trailing end) of the bottom surgical fastener 20A so that the distal surface 72 of the ramp 70 of the insertion tool 60 (FIG. 3C) engages the center section 44 of the crown 42 (FIG. 1E) located at the proximal end of the surgical fastener.

Figure 5C:
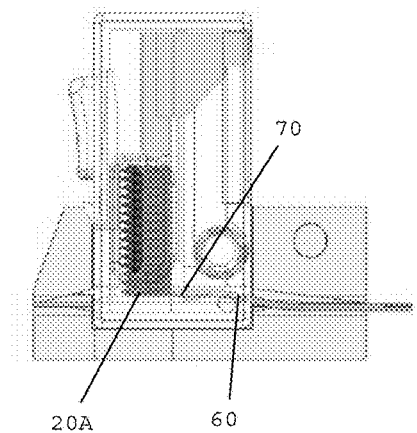

Referring to FIG. 5C, in one embodiment, the ramp 70 of the insertion tool 60 (FIG. 3C) engages the crown 42 (FIG. 1E) at the proximal end of the bottom surgical fastener 20A to strip the bottom surgical fastener 20A from the bottom of the stack of surgical fasteners.

Figure 5D:
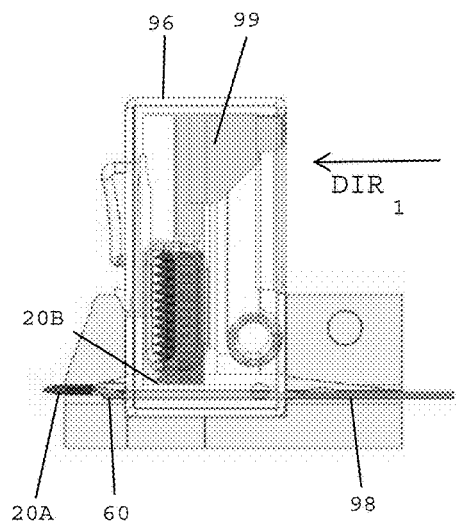

Referring to FIG. 5D, in one embodiment, the center section 44 and the first and second laterally extending flanges 46A, 46B of the crown 42 (FIG. 1E) at the proximal end of the surgical fastener 20A are disposed between the opposing C-shaped projections 66A, 66B at the distal end 64 of the insertion tool 60 (FIG. 3C). The firing rod 98 and the insertion tool 60 continue to move in a distal direction designed $DIR_1$ for advancing the surgical fastener 20A distally toward the distal end of the applicator instrument. The cartridge 96 preferably has a spring mechanism 99 for advancing the next surgical fastener 20B in the stack into alignment with a channel for the next firing cycle.

Figures 1, 5D:
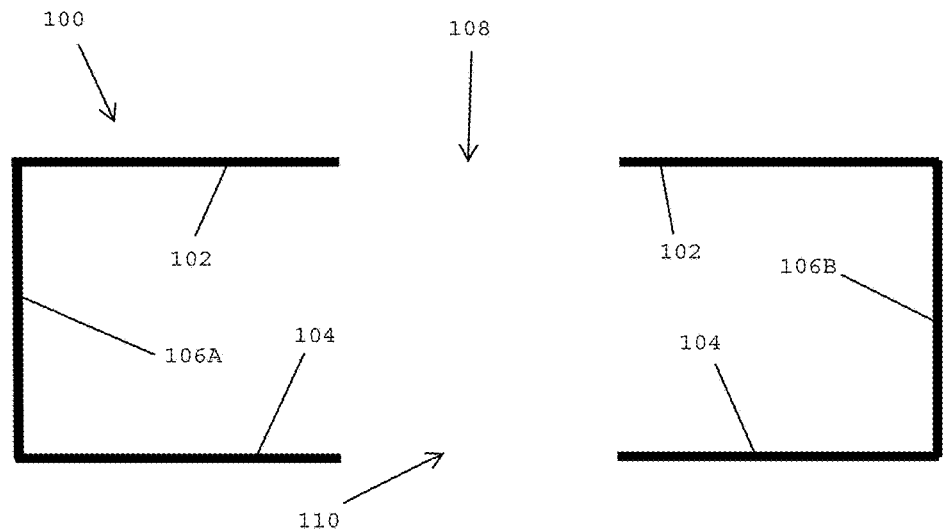
Figures 2, 5D:
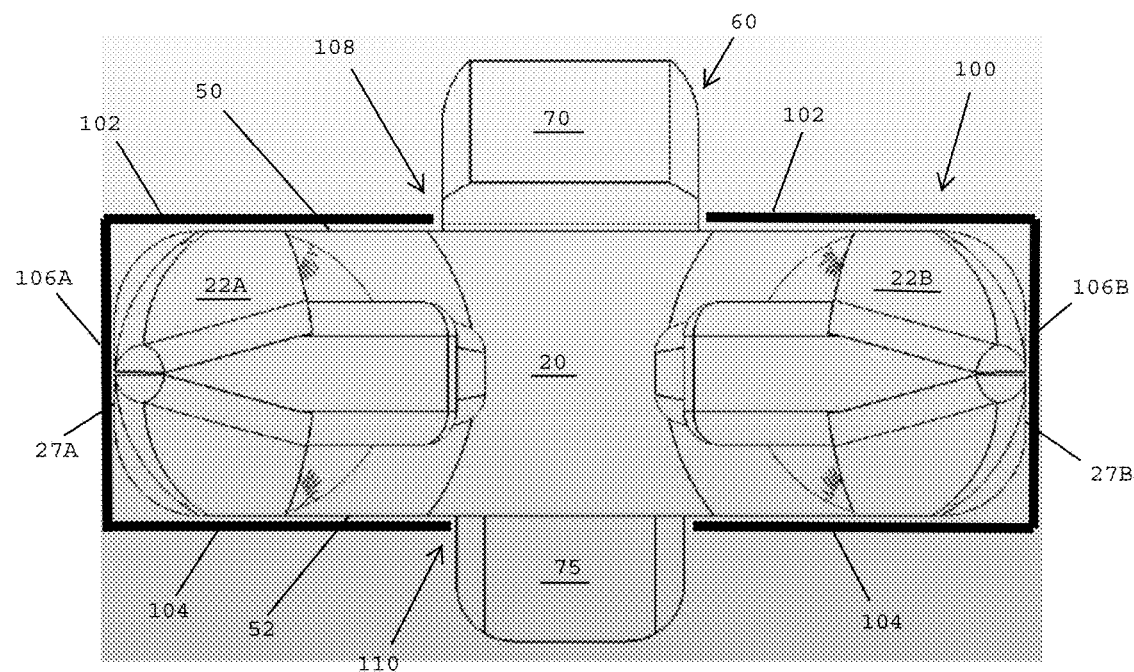

Referring to FIG. 5D-1, in one embodiment, an applicator instrument for dispensing surgical fasteners preferably has an elongated channel 100 for guiding a surgical fastener and an insertion tool joined with the surgical fastener toward the distal end of the applicator instrument. In one embodiment, the elongated channel 100 includes a top wall 102, a bottom wall 104, and side walls 106A, 106B that extend between the top wall and the bottom wall. The top wall 102 of the elongated channel 100 has an elongated top notch 108 formed therein and the bottom wall 104 has an elongated bottom notch 110 formed therein. In one embodiment, the elongated top and bottom notches 108, 110 oppose one another and are in alignment with one another.

Referring to FIG. 5D-2, in one embodiment, the distal end of the insertion tool 60 engages the proximal end of the surgical fastener 20 for advancing the surgical fastener toward the distal end of the applicator instrument. In one embodiment, the flat top surface 50 of the surgical fastener 20 and the flat top surface 80 (FIG. 4C) of the insertion tool 60 are opposed by the top wall 102 of the elongated channel 100, and the flat bottom surface 52 of the surgical fastener 20 and the flat bottom surface 92 (FIG. 4D) of the insertion tool 60 are opposed by the bottom wall 104 of the elongated channel 100. In addition, the flat side surface 27A of the first leg 22A of the surgical fastener 20 and the first flat side surface 94A (FIG. 4C) of the insertion tool 60 are opposed by the first side wall 106A of the elongated channel 100, and the flat side surface 27B of the second leg 22B of the surgical fastener 20 and the second flat side surface 94B (FIG. 4D) of the insertion tool 60 are opposed by the second side wall 106B of the elongated channel 100. The opposing top wall 102, bottom wall 104, and side walls 106A, 106B preferably guide and control the orientation of the surgical fastener 20 and the insertion tool 60 as the joined elements move distally through the elongated channel 100.

In one embodiment, as the insertion tool 60 moves distally through the elongated channel 100, the stripper ramp 70 slides through the elongated top notch 108 in the top wall 102 of the elongated channel 100 and the attachment flange 75 slides through the elongated bottom notch 110 in the bottom wall 104 of the elongated channel 100. The registration of the stripper ramp 70 with the elongated top notch 108 and the attachment flange 75 with the elongated bottom notch 110 preferably provides further control over the orientation and stability of the surgical fastener 20 and insertion tool 60 as the joined elements move distally through the elongated channel 100.

Figure 6A:
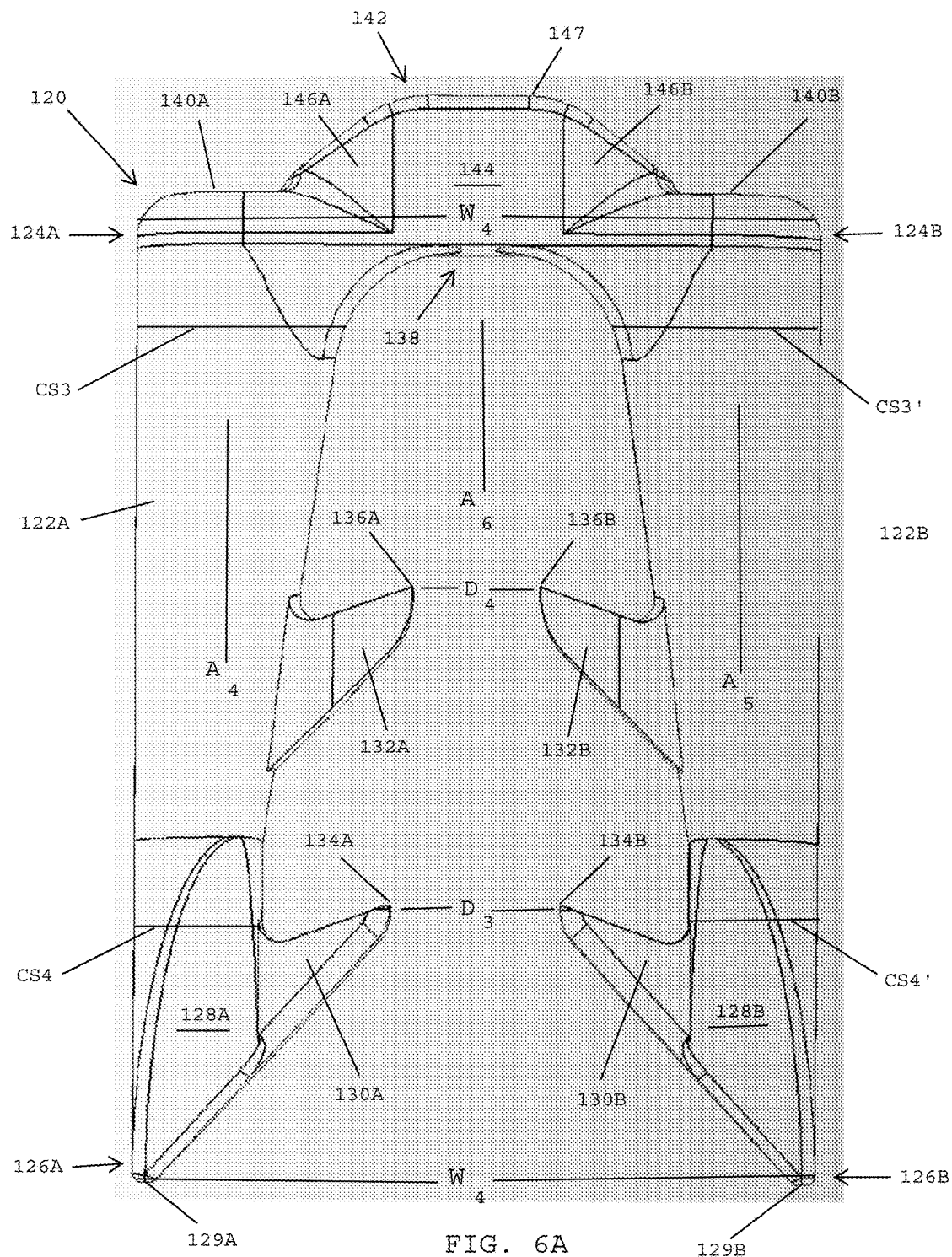
FIGS. 6A-6F show a surgical fastener used to secure prosthetic devices to tissue, in accordance with a second embodiment.
Figure 6B:
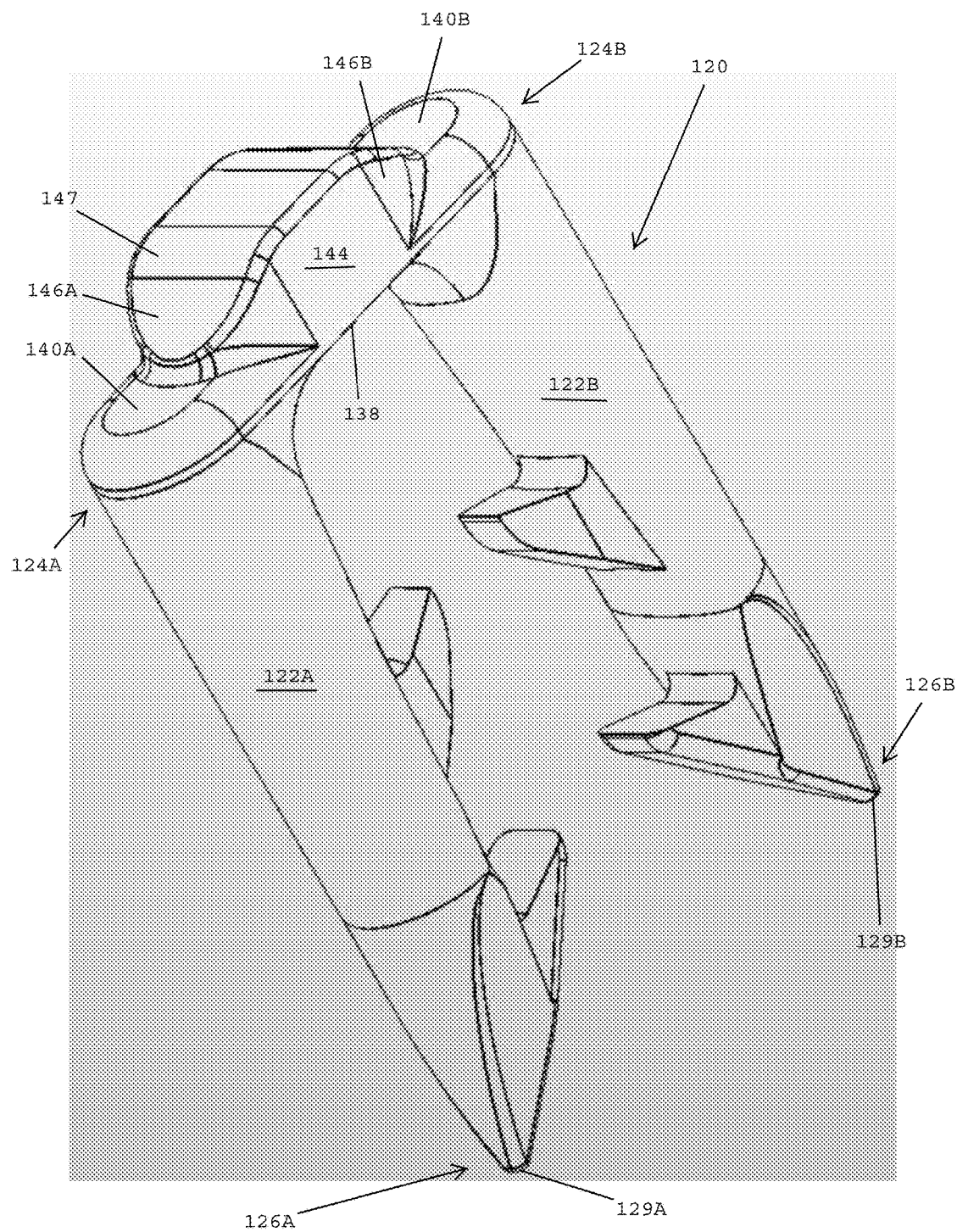
Figure 6C:
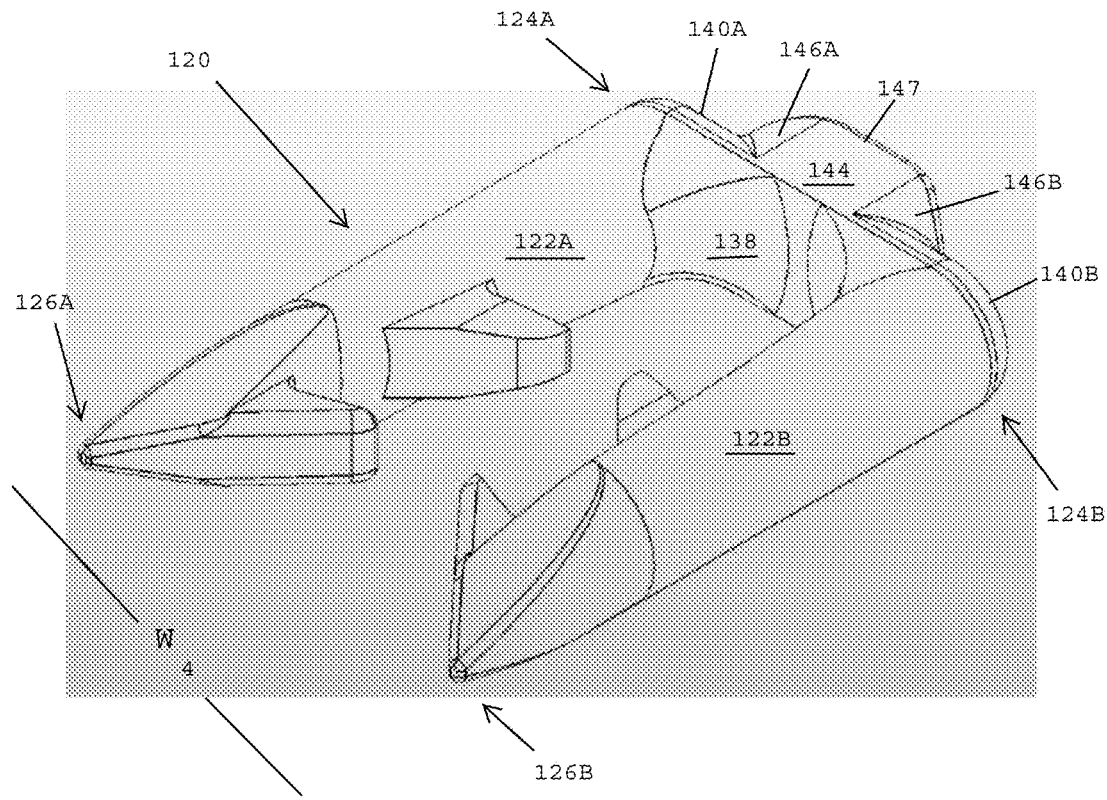

Referring to FIG. 6A-6C, in one embodiment, a surgical fastener 120 has one or more of the structural features disclosed above in the embodiment shown in FIGS. 1A-1H. In one embodiment, the surgical fastener includes first and second legs 122A, 122B that are interconnected at their proximal ends by a bridge 138. In one embodiment, a proximal side of the bridge 138 defines a major surface 140 including sections 140A, 140B that extend over the proximal ends 124A, 124B of the respective first and second legs 122A, 122B. A proximal end of the bridge 138 includes a crown 142 having a center section 144 and first and second laterally extending flanges 146A, 146B that project laterally from the center section 144. The proximal-most surface of the crown 142 includes a convexly curved surface 147 that extends over the center section 144 and the first and second laterally extending flanges 146A, 146B. In one embodiment, the distal end of an insertion tool or a firing rod engages the crown 142 for applying an insertion force on the proximal end of the surgical fastener and controlling the orientation of the surgical fastener 120 as it is advanced distally in an applicator instrument.

In one embodiment, the distal end of the insertion tool has a shape that in a negative of the crown 142 so that the insertion tool can securely engage the proximal end of the surgical fastener for controlling the orientation of the surgical fastener as it moves distally through the applicator instrument.

Referring to FIG. 6A, in one embodiment, the surgical fastener 120 has a width $W_4$ at the proximal ends 124A, 124B of the legs 122A, 122B that equals the width $W_4$ at the distal ends 126A, 126B of the legs 122A, 122B. In one embodiment, the width $W_4$ of the surgical fastener 120 remains constant between the proximal ends 124A, 124B and the distal ends 126A, 126B of the respective first and second legs 122A, 122B. In one embodiment, the bridge 138 has a length that matches the width $W_4$.

In one embodiment, the first leg 122A of the surgical fastener 120 extends along a first longitudinal axis $A_4$, and the second leg 122B of the surgical fastener 120 extends along a second longitudinal axis $A_5$. In one embodiment, the surgical fastener has a central axis $A_6$ that bisects the surgical fastener 120 into two halves including a first half having the first leg 122A with distal and proximal barbs 130A, 132A, and a second half having the second leg 122B with distal and proximal barbs 130B, 132B. The central axis $A_6$ is preferably parallel to the first longitudinal axis $A_4$ of the first leg 122A and the second longitudinal axis $A_5$ of the second leg 122B. In one embodiment, the distance $D_3$ between the distal barbs 130A, 130B is greater than the distance $D_4$ between the proximal barbs 132A, 132B. In one embodiment, the distance $D_3$ between inner tips 134A, 134B of the respective distal barbs 130A, 130B is about 0.040 inches and the distance $D_4$ between the inner tips 136A, 136B of the proximal barbs 132A, 132B is about 0.030 inches.

In one embodiment, the first leg 122A desirably tapers inwardly between the proximal end 124A of the first leg 122A and the distal end 126A of the first leg 122A so that a first cross sectional area CS3 adjacent the proximal end 124A of the first leg is greater than a second cross sectional area CS4 adjacent the distal end 126A of the first leg 122A. In one embodiment, the largest cross sectional area of the first leg is adjacent the proximal end 124A of the first leg and the first leg tapers inwardly between the proximal end and the distal end thereof.

In one embodiment, the second leg 122B desirably tapers inwardly between the proximal end 124B of the second leg 122B and the distal end 126B of the second leg 122B so that a first cross sectional area CS3' adjacent the proximal end 124B of the second leg is greater than a second cross sectional area CS4' adjacent the distal end 126B of the second leg 122B. In one embodiment, the largest cross sectional area of the second leg is adjacent the proximal end 124B of the second leg and the second leg tapers inwardly between the proximal end and the distal end thereof.

Figure 6D:
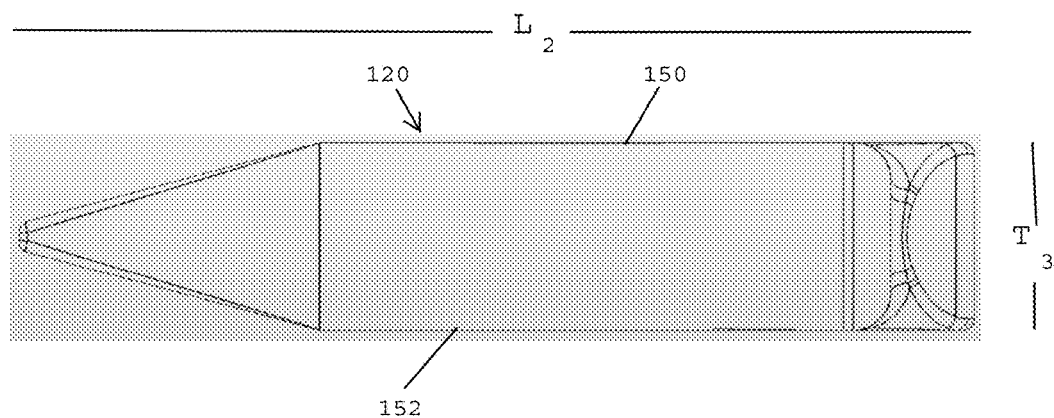

Referring to FIGS. 6A and 6D, in one embodiment, the surgical fastener 120 has a length $L_2$ of about 0.248 inches, a width $W_4$ of about 0.160 inches, and a thickness $T_3$ of about 0.050 inches. In one embodiment, the width $W_4$ of the surgical fastener 120 is the same at the proximal and distal ends thereof, and the width $W_4$ remains constant between the proximal and distal ends of the surgical fastener. In one embodiment, although the cross sectional area of the legs decreases between the proximal and distal ends of the respective first and second legs 122A, 122B, the width $W_4$ of the surgical fastener remains constant between the proximal and distal ends of the first and second legs.

Figure 6E:
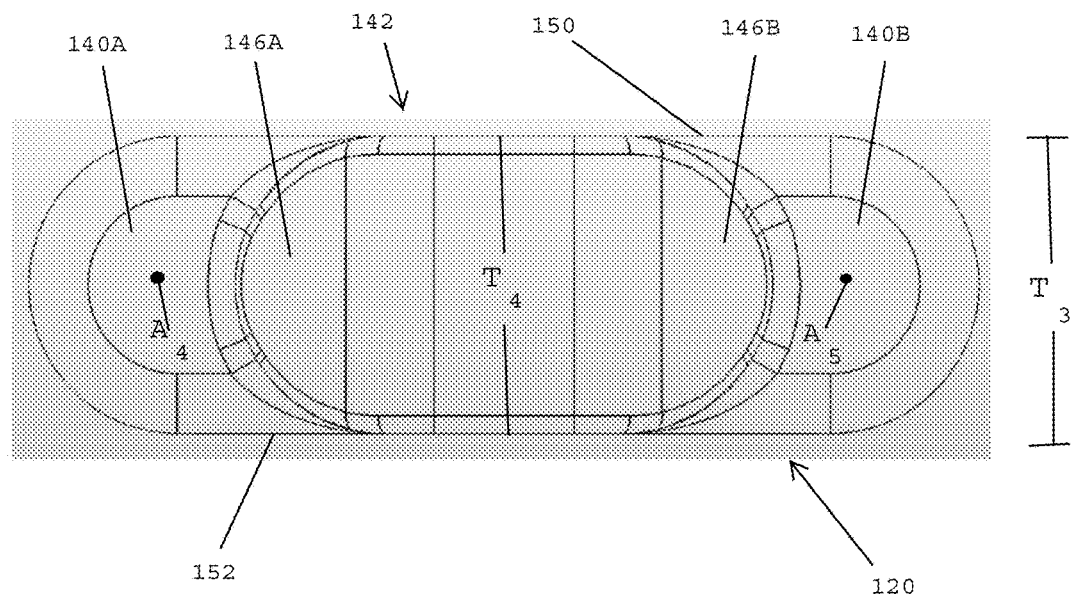

Referring to FIG. 6E, in one embodiment, the center section 144 of the crown 142 defines a thickness $T_4$ that equals the thickness $T_3$ of the surgical fastener 120.

Referring to FIGS. 6B and 6E, in one embodiment, the crown 142 at the proximal end of the surgical fastener 120 preferably includes the center section 144 and the first and second laterally extending flanges 146A, 146B that extend laterally from the center section 144. The surfaces 140A, 140B at the proximal ends of the respective first and second legs 122A, 122B desirably extend around the sides of the respective first and second laterally extending flanges 146A, 146B. In one embodiment, the first section 140A of the major surface 140 extending around the first laterally extending flange 146A has a C-shape, and the second section 140B of the major surface 140 extending around the second laterally extending flange 146B has a C-shape. In one embodiment, the C-shaped first and second sections 140A, 140B of the major surface 140 have the same configuration and oppose one another on opposite sides of the center section 144. In one embodiment, the C-shaped sections 140A, 140B are aligned with the longitudinal axes $A_4$, $A_5$ of the respective first and second legs 122A, 122B.

Figure 6F:
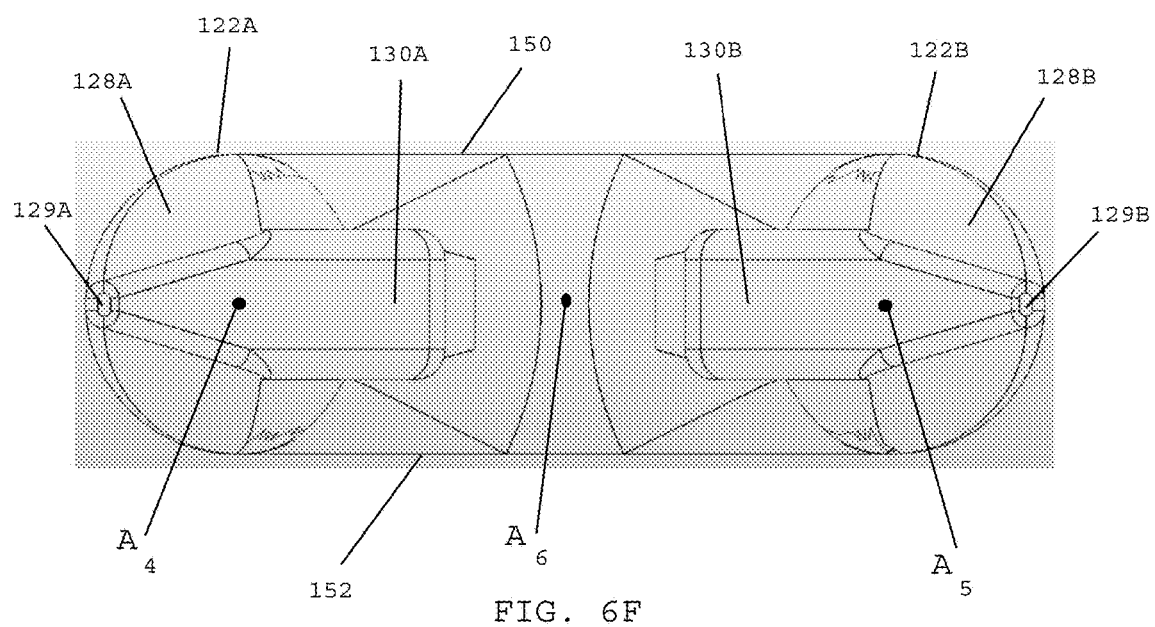

Referring to FIGS. 6A and 6F, in one embodiment, the first leg 122A of the surgical fastener 120 has a distal end 126A with the first insertion tip 128A having the distal-most point 129A. The first insertion tip 128A is skewed outwardly relative to the longitudinal axis $A_4$ of the first leg 122A. The first leg 122A includes the distal barb 130A that extends inwardly toward the second leg 122B of the surgical fastener 120. The second leg 122B has a distal end 126B with the second insertion tip 128B having the distal-most point 129B. The second insertion tip 128B is skewed outwardly relative to the longitudinal axis $A_5$ of the second leg 122B. The second leg 122B includes the distal barb 130B that extends inwardly toward the first leg 122A. The distal barbs 130A, 130B extend toward one another, oppose one another, and are aligned with one another adjacent the distal ends 126A, 126B of the respective first and second legs 122A, 122B. The central axis $A_6$ bisects the surgical fastener into a first half including the first leg 122A and a second half including the second leg 122B.

Referring to FIGS. 6D and 6E, in one embodiment, the surgical fastener 120 desirably includes a first major surface 150 that extends over a top side of the surgical fastener 120 and a second major surface 152 that extends over an underside of the surgical fastener 120. In one embodiment, the first and second major surfaces 150, 152 are flat. In one embodiment, the first major surface 150 extends over the center section 144 and the first and second legs 122A, 122B of the surgical fastener. In one embodiment, the second major surface 152 and extends over the opposite side of the center section 144 and the opposite sides of the first and second legs 122A, 122B of the surgical fastener.

Figure 7A:
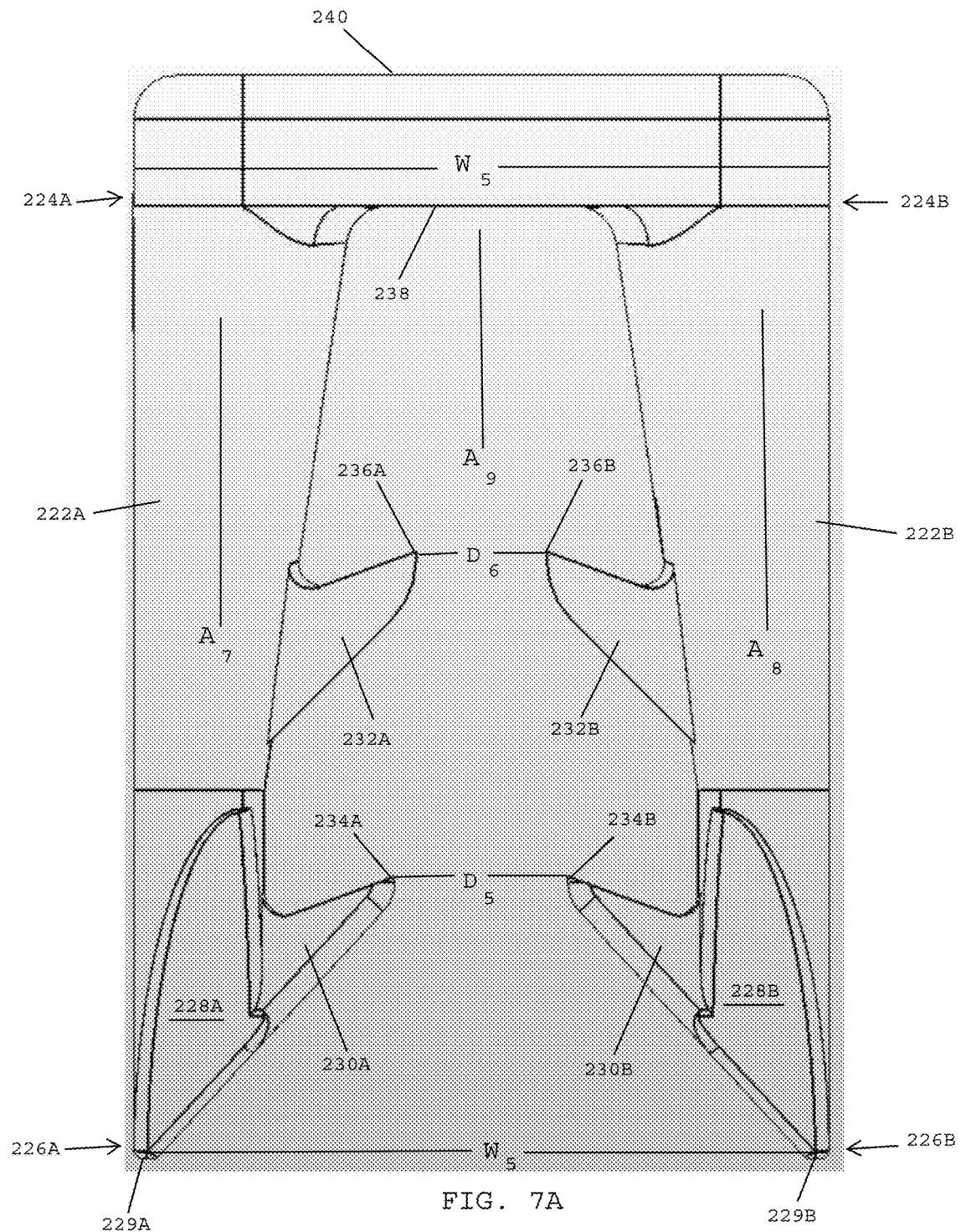
FIGS. 7A-7F show a surgical fastener used to secure prosthetic devices to tissue, in accordance with a third embodiment.
Figure 7B:
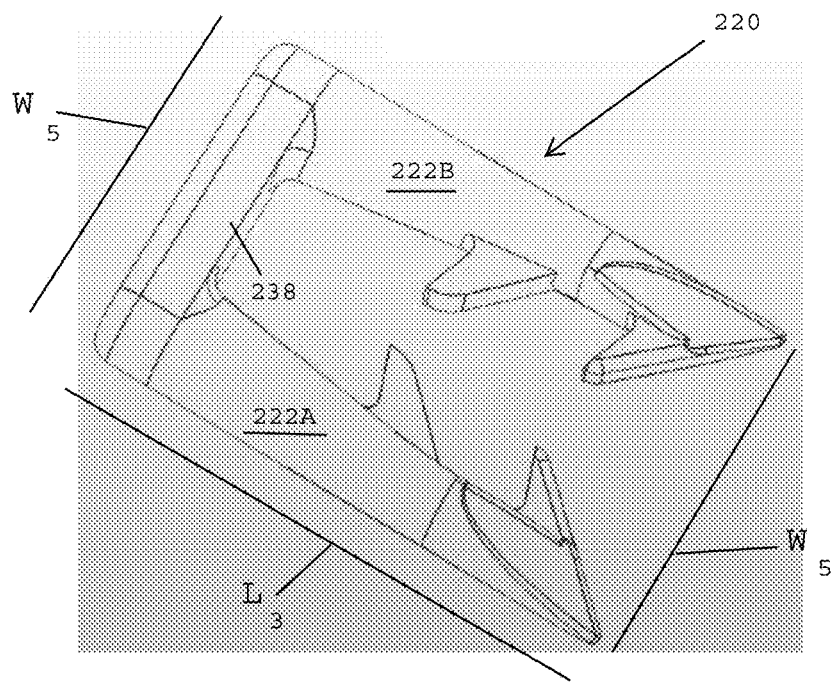
Figure 7C:
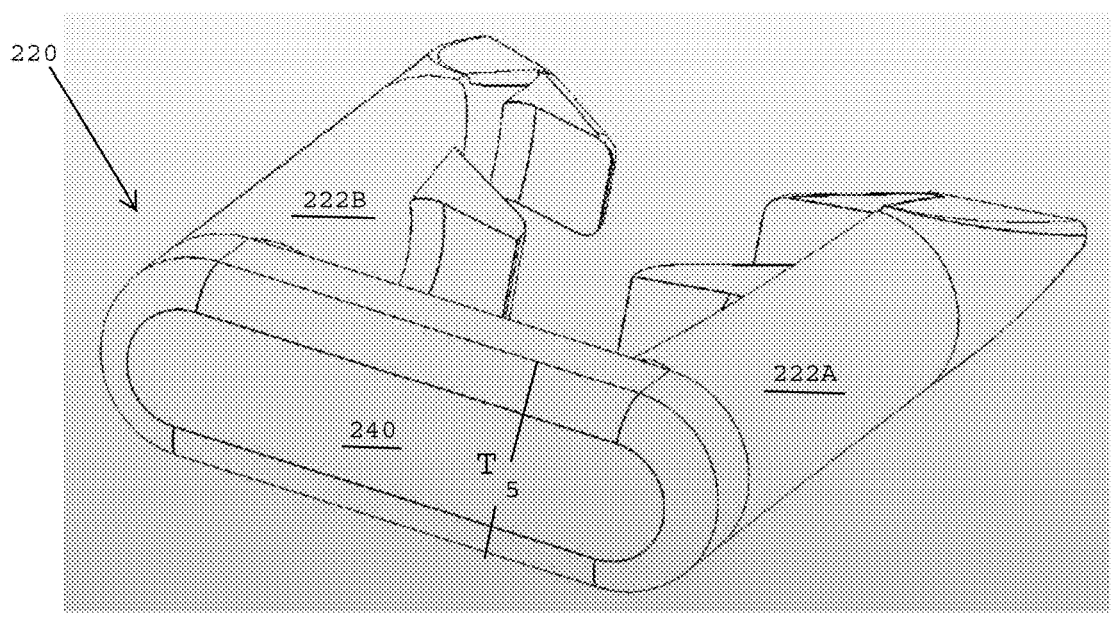
Figure 7D:
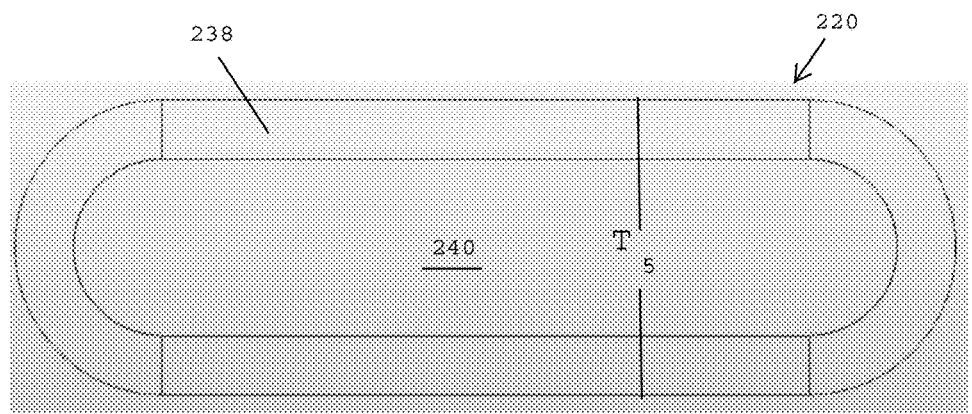

Referring to FIGS. 7A-7C, in one embodiment, a surgical fastener 220 for securing prosthetic devices to tissue preferably includes a first leg 222A having a proximal end 224A and a distal end 226A. The first leg 222A desirably tapers inwardly between the proximal end 224A of the first leg 222A and the distal end 226A of the first leg 22A so that a first cross sectional area CS5 adjacent the proximal end 224A of the first leg is greater than a second cross sectional area CS6 adjacent the distal end 226A of the first leg 222A. In one embodiment, the largest cross sectional area of the first leg is adjacent the proximal end of the first leg and the first leg tapers inwardly between the proximal end and the distal end thereof.

In one embodiment, the first leg 222A extends along a first longitudinal axis $A_7$. In one embodiment, the first leg 222A includes an insertion tip 228A located at the distal end 226A of the first leg 222A with a point 229A being located at the distal-most end of the first leg. In one embodiment, the insertion tip 228A is asymmetrical so that it skews outwardly relative to the longitudinal axis $A_7$ of the first leg 222A.

In one embodiment, the surgical fastener 220 includes a second leg 222B having a proximal end 224B and distal end 226B. The second leg 222B desirably has a first cross sectional area CS5' adjacent the proximal end 224B that is greater than a second cross sectional CS6' adjacent the distal end 226B. The second leg 222B has an insertion tip 228B located at the distal end thereof and a point 229B located at the distal-most end of the second leg 222B. In one embodiment, the second leg 222B extends along an axis $A_8$ that is parallel to the axis $A_7$ of the first leg 222A. In one embodiment, the insertion tip 228B on the second leg 222B is asymmetrical and skews outwardly relative to the second axis $A_8$ of the second leg 222B.

In one embodiment, the first leg 222A includes a distal barb 230A located at the distal end 226A of the first leg 222A. In one embodiment, the distal barb 230A is positioned adjacent the distal end 226A of the first leg 222A and is proximal to the point 229A. The distal barb 230A preferably extends inwardly toward the second leg 222B. In one embodiment, the first leg 222A has a proximal barb 232A that also extends inwardly toward the second leg 222B. In one embodiment, the proximal barb 232A on the first leg 222A is located between the proximal end 224A of the first leg 222A and the distal barb 230A. In one embodiment, the proximal barb 232A is located about halfway between the proximal end 224A and the distal end 226A of the first leg 222A.

In one embodiment, the second leg 222B of the surgical fastener 220 preferably includes a distal barb 230B that extends inwardly toward the first leg 222A. In one embodiment, the distal barb 230B is positioned adjacent the distal end 226B of the second leg 222B and is proximal to the point 229B. The distal barb 230A preferably extends inwardly toward the second leg 222B. In one embodiment, the distal barbs 230A, 230B on the respective first and second legs 222A, 222B oppose one another, extend toward one another, and are aligned with one another along the lengths of the respective first and second legs 222A, 222B.

In one embodiment, the second leg 222B includes a proximal barb 232B that extends inwardly toward the first leg 222A. In one embodiment, the proximal barbs 232A, 232B on the respective first and second legs 222A, 222B extend toward one another, oppose one another, and are aligned with one another along the lengths of the respective first and second legs 222A, 222B.

In one embodiment, the surgical fastener 220 extends along a central axis $A_9$ that bisects the surgical fastener 220 into a first half including the first leg 222A and the associated barbs 230A, 232A, and a second half including the second leg 222B and the associated barbs 230B, 22B. The central axis $A_9$ is preferably parallel to the first axis $A_7$ of the first leg 222A and the second axis $A_8$ of the second leg 222B. In one embodiment, the central axis $A_9$ bisects the surgical fastener 220 into two equally sized halves. In one embodiment, the central axis $A_9$ is desirably equidistant from the first axis $A_7$ of the first leg 222A and the second axis $A_8$ of the second leg 222B.

In one embodiment, the distal barb 230A on the first leg 222A has an inner tip 234A and the distal barb 230B on the second leg 222B has an inner tip 234B. The respective innermost tips 234A, 234B define a distance $D_5$ that extends along an axis that is perpendicular to the central axis $A_9$ of the surgical fastener 220.

In one embodiment, the proximal barb 232A on the first leg 222A has an inner tip 236A and the proximal barb 232B on the second leg 222B has an inner tip 236B. The inner tips 236A, 236B define a distance $D_6$ that extends along an axis that is perpendicular to the central axis $A_9$ of the surgical fastener 220. In one embodiment, the distance $D_5$ between the inner tips 234A, 234B of the respective distal barbs 230A, 230B is greater than the distance $D_6$ between the inner tips 236A, 236B of the proximal barbs 232A, 232B. In one embodiment, the distance $D_5$ is about 0.040 inches and the distance $D_6$ is about 0.030 inches.

Referring to FIGS. 7A-7C, in one embodiment, the surgical fastener 220 includes a bridge 238 located at a proximal end of the surgical fastener that interconnects the proximal ends 224A, 224B of the respective first and second legs 222A, 222B. The central axis $A_9$ desirably bisects the bridge 238. In one embodiment, the bridge 238 includes a major surface 240, such as a flat surface, that extends adjacent the proximal ends 224A, 224B of the first and second legs 222A, 222B. In one embodiment, the major surface 240 preferably defines a proximal-most surface on the surgical fastener 220. In one embodiment, the major surface 240 is engaged by a leading end of a firing rod or the leading end of an insertion tool secured to a firing rod for applying an insertion force onto the surgical fastener and controlling the orientation of the surgical fastener as the surgical fastener is dispensed from an applicator instrument.

Referring to FIGS. 7A-7D, in one embodiment, the surgical fastener 220 has a length $L_3$ of about 0.248 inches, a width $W_5$ of about 0.160 inches, and a thickness $T_5$ of about 0.050 inches. In one embodiment, the width $W_5$ of the surgical fastener 220 is the same at the proximal and distal ends thereof, and the width remains constant between the proximal and distal ends of the surgical fastener. In one embodiment, the width $W_5$, defined by the distance between the outer surfaces of the first and second legs 222A, 222B at the proximal end of the surgical fastener, equals the distance between the outer surfaces of the insertion tips 228A, 228B at the distal ends of the first and second legs 222A, 222B. As noted above, in one embodiment, the cross sectional areas of the legs decreases between the proximal and distal ends of the respective first and second legs 222A, 222B, however, the width $W_5$ of the surgical fastener remains constant between the proximal and distal ends of the first and second legs.

Figure 7E:
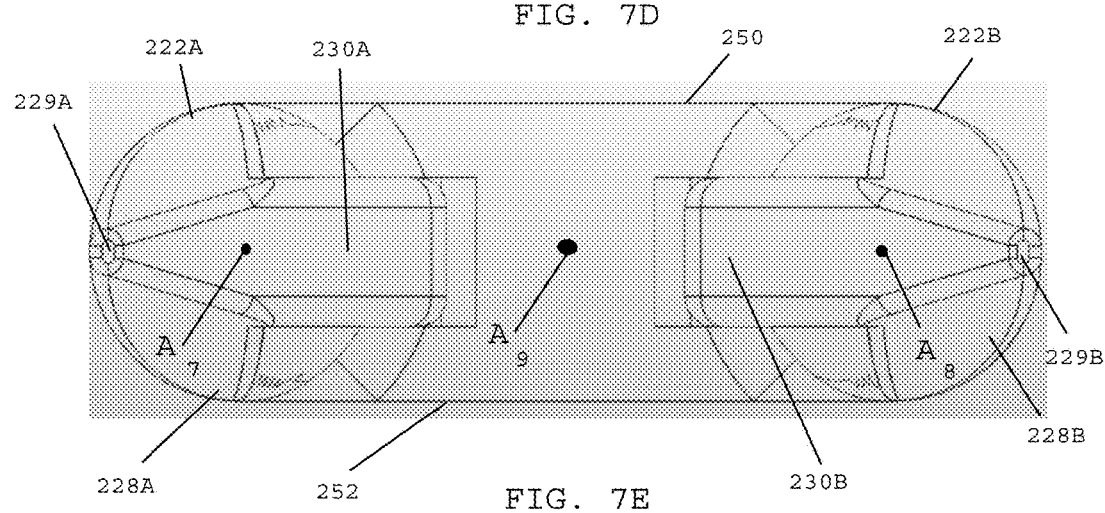

Referring to FIGS. 7A and 7E, in one embodiment, the first leg 222A of the surgical fastener 220 has a distal end 226A with the first insertion tip 228A having the distal-most point 229A. The first insertion tip 228A is skewed outwardly relative to the longitudinal axis $A_7$ of the first leg 222A. The first leg 222A includes the distal barb 230A that extends inwardly toward the second leg 222B of the surgical fastener 220. The second leg 222B has a distal end 226B with the second insertion tip 228B having the distal-most point 229B. The second insertion tip 228B is skewed outwardly relative to the longitudinal axis $A_8$ of the second leg 222B. The second leg 222B includes the distal barb 230B that extends inwardly toward the first leg 222A. The distal barbs 230A, 230B extend toward one another, oppose one another, and are aligned with one another adjacent the distal ends 226A, 226B of the respective first and second legs 222A, 222B. The central axis $A_9$ bisects the surgical fastener into a first half including the first leg 222A and a second half including the second leg 222B.

Figure 7F:
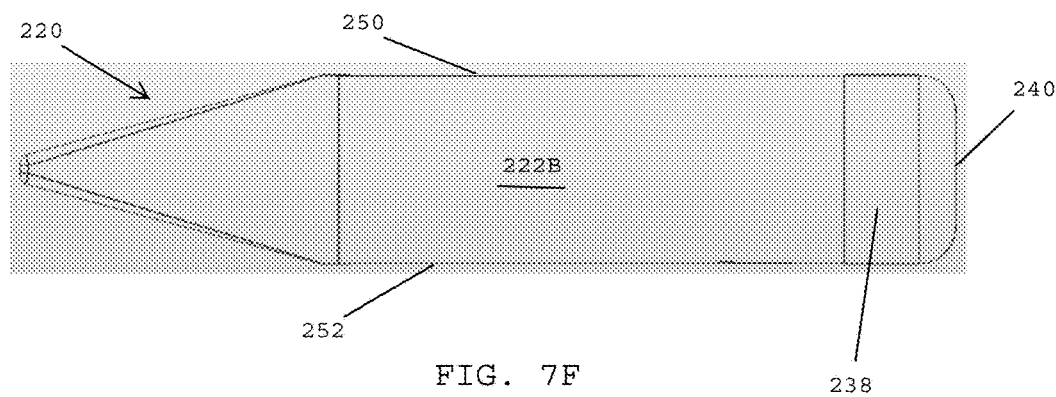

Referring to FIGS. 7E and 7F, in one embodiment, the surgical fastener 220 desirably includes a first major surface 250 that extends over a top side of the surgical fastener 220 and a second major surface 252 that extends over an underside of the surgical fastener 220. In one embodiment, the first major surface 250 is flat and extends over the bridge 238 and the first and second legs 222A, 222B of the surgical fastener. In one embodiment, the second major surface 252 is also flat and extends over opposite sides of the bridge 238 and the first and second legs 222A, 222B.

Figure 8A:
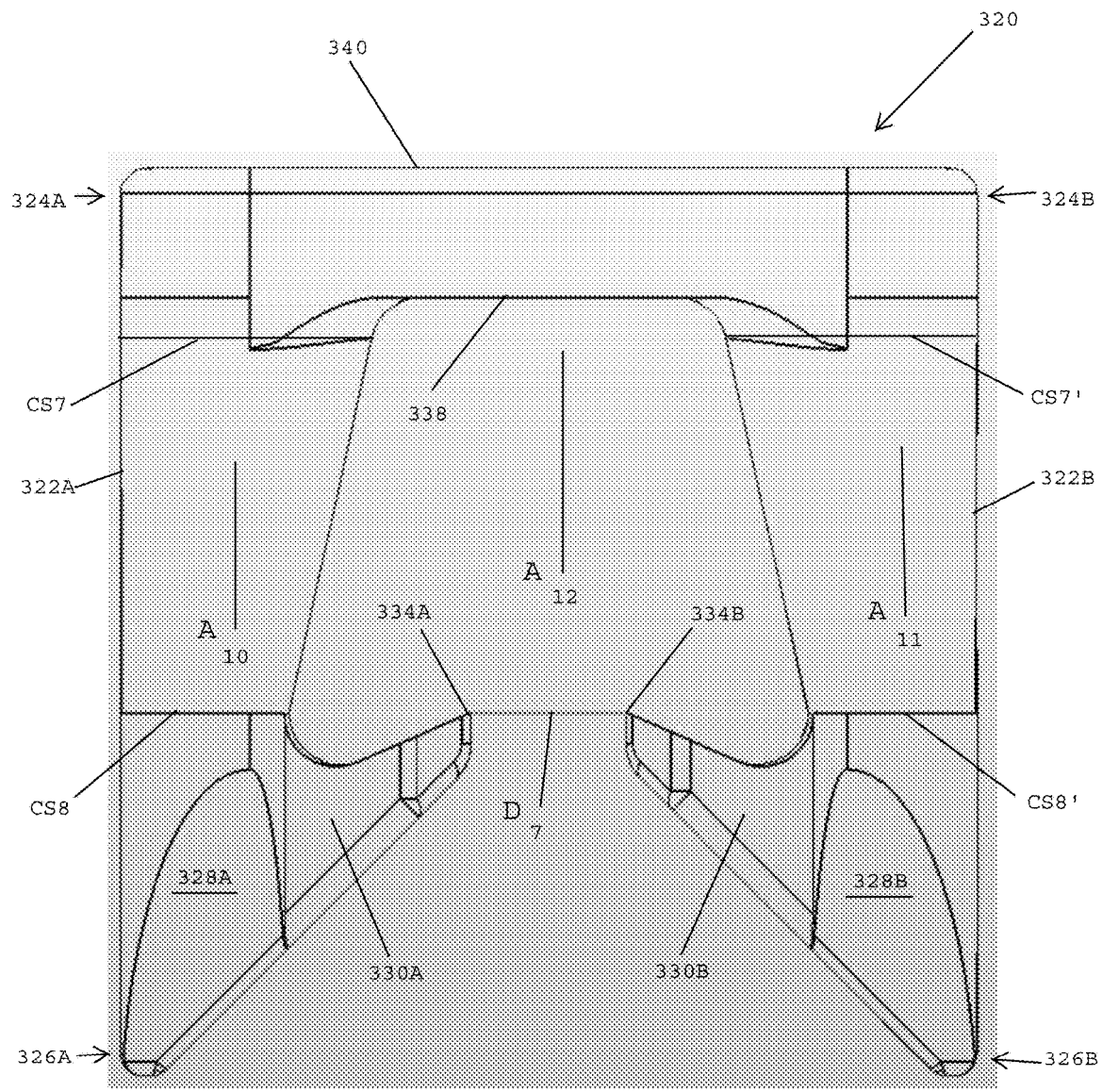
FIGS. 8A-8F show a surgical fastener used to secure prosthetic devices to tissue, in accordance with a fourth embodiment.
Figure 8B:
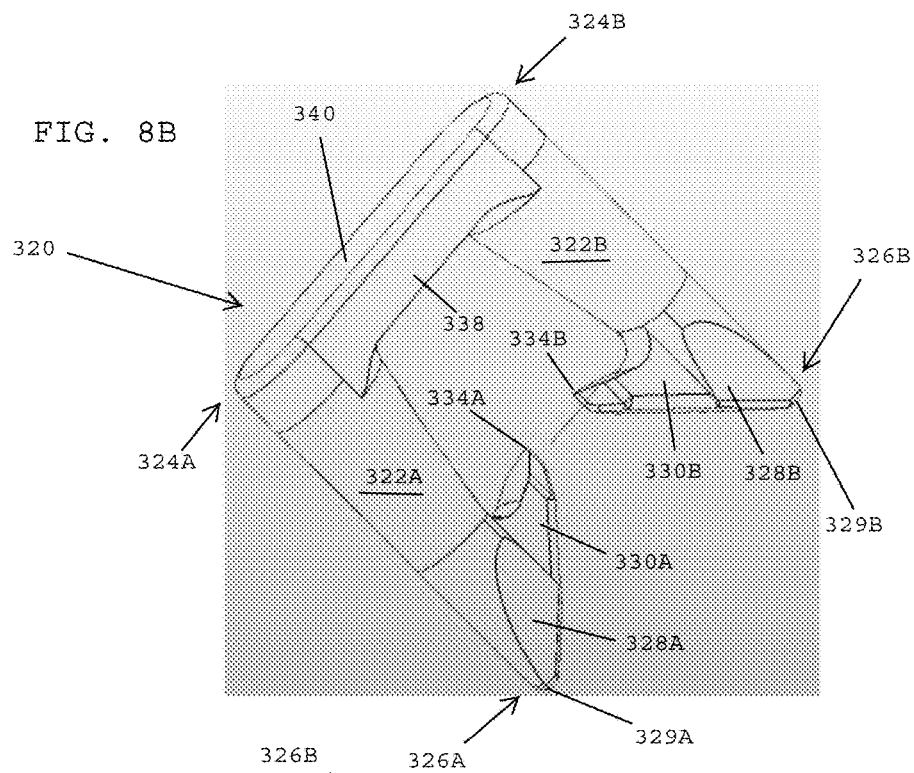
Figure 8C:
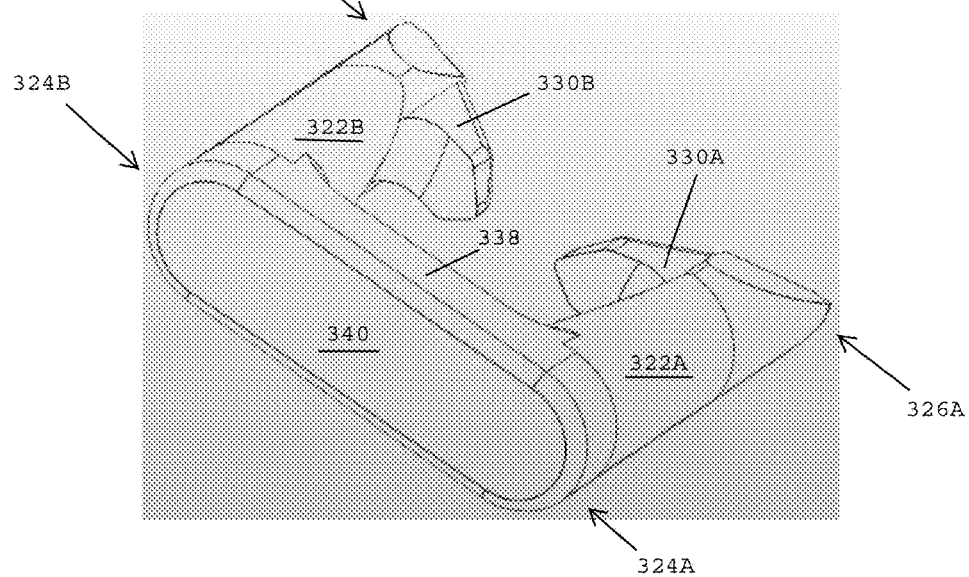
Figure 8D:
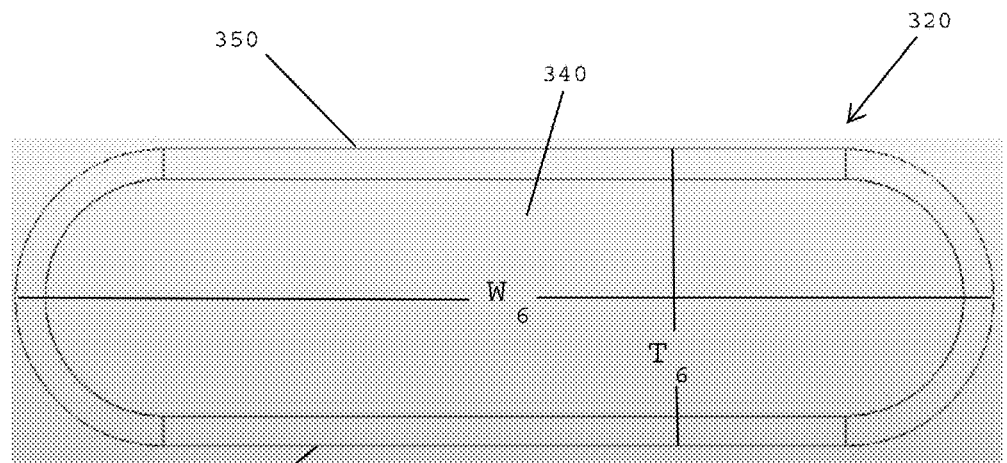

Referring to FIGS. 8A-8C, in one embodiment, a surgical fastener 320 for securing prosthetic devices to tissue preferably includes a first leg 322A having a proximal end 324A and a distal end 326A. The first leg 322A desirably tapers inwardly between the proximal end 324A of the first leg 322A and the distal end 326A of the first leg 322A so that a first cross sectional area CS7 adjacent the proximal end 324A of the first leg is greater than a second cross sectional area CS8 adjacent the distal end 326A of the first leg 322A. In one embodiment, the largest cross sectional area of the first leg is adjacent the proximal end of the first leg and the first leg tapers inwardly between the proximal end and the distal end thereof.

In one embodiment, the first leg 322A extends along a first longitudinal axis $A_{10}$. In one embodiment, the first leg 322A includes an insertion tip 328A located at the distal end 226A of the first leg 322A with a distal-most point 329A being located at the distal end of the first leg. In one embodiment, the insertion tip 328A is asymmetrical so that it skews outwardly relative to the longitudinal axis $A_{10}$ of the first leg 322A.

In one embodiment, the surgical fastener 320 includes a second leg 322B having a proximal end 324B and distal end 326B. The second leg 322B desirably has a first cross sectional area CS7' adjacent the proximal end 324B that is greater than a second cross sectional CS8' adjacent the distal end 326B. The second leg 322B has an insertion tip 328B located at the distal end thereof and a distal-most point 329B located at the distal end of the second leg 322B. In one embodiment, the second leg 322B extends along a longitudinal axis $A_{11}$ that is parallel to the longitudinal axis $A_{10}$ of the first leg 322A. In one embodiment, the insertion tip 328B on the second leg 322B is asymmetrical and skews outwardly relative to the second longitudinal axis $A_{11}$ of the second leg 322B.

In one embodiment, the first leg 322A includes a barb 330A located adjacent the distal end 326A of the first leg 322A. In one embodiment, the barb 330A is positioned adjacent the distal end 326A of the first leg 322A and is proximal to the distal-most point 329A. The barb 330A preferably extends inwardly toward the second leg 322B.

In one embodiment, the second leg 322B of the surgical fastener 320 preferably includes a barb 330B adjacent the distal end of the first leg that extends inwardly toward the first leg 322A. In one embodiment, the barbs 330A, 330B on the respective first and second legs 322A, 322B oppose one another, extend toward one another, and are aligned with one another along the lengths of the respective first and second legs 322A, 322B.

In one embodiment, the surgical fastener 320 extends along a central axis $A_{12}$ that bisects the surgical fastener 320 into a first half including the first leg 322A and the associated barb 230A, and a second half including the second leg 322B and the associated barb 330B. The central axis $A_{12}$ is preferably parallel to the first longitudinal axis $A_{10}$ of the first leg 322A and the second longitudinal axis $A_{11}$ of the second leg 322B. In one embodiment, the central axis $A_{12}$ is desirably equidistant from the first axis $A_{10}$ of the first leg 322A and the second axis $A_{11}$ of the second leg 322B.

In one embodiment, the barb 330A on the first leg 322A has an inner tip 334A and the barb 230B on the second leg 322B has an inner tip 334B. The respective inner tips 334A, 334B define a distance $D_7$ that extends along an axis that is perpendicular to the central axis $A_{12}$ of the surgical fastener 320. In one embodiment, the distance $D_7$ is about 0.040 inches.

In one embodiment, the surgical fastener 320 includes a bridge 338 that interconnects the proximal ends 324A, 324B of the respective first and second legs 322A, 322B. The central axis $A_{12}$ desirably bisects the bridge 338. In one embodiment, the bridge 338 includes a major surface 340, such as a flat surface, that defines a proximal-most surface on the surgical fastener 320. In one embodiment, the major surface 340 is engaged by a leading end of a firing rod or an insertion tool secured to a firing rod for applying an insertion force onto the surgical fastener and for controlling the orientation of the surgical fastener as the surgical fastener is dispensed from an applicator instrument.

Referring to FIGS. 8A, and 8D-8F, in one embodiment, the surgical fastener 320 has a length $L_4$ of about 0.248 inches, a width $W_6$ of about 0.160 inches, and a thickness $T_6$ of about 0.050 inches. In one embodiment, the width $W_6$ of the surgical fastener 320 is the same at the proximal and distal ends thereof, and the width remains constant between the proximal and distal ends of the surgical fastener. In one embodiment, the width $W_6$, defined by the distance between the outer surfaces of the first and second legs 322A, 322B at the proximal end of the surgical fastener, equals the distance between the outer surfaces of the insertion tips 328A, 328B at the distal ends 326A, 326B of the first and second legs 322A, 322B. As noted above, in one embodiment, the cross sectional areas of the legs decrease between the proximal and distal ends of the respective first and second legs 322A, 322B, however, the width $W_6$ of the surgical fastener remains constant between the proximal and distal ends of the first and second legs.

Figure 8E:
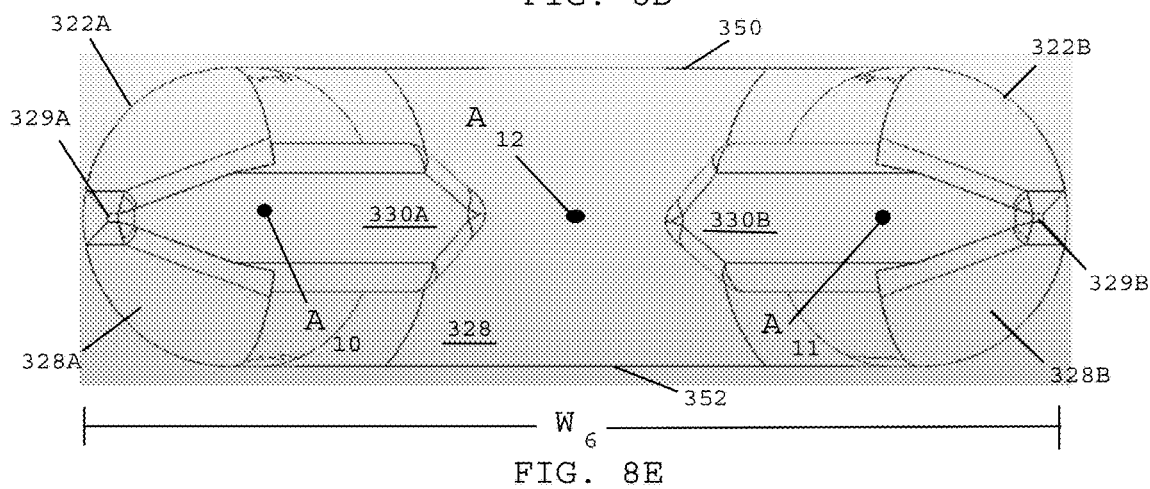

Referring to FIGS. 8A and 8E, in one embodiment, the first leg 322A of the surgical fastener 320 has a distal end 326A with the first insertion tip 328A having the distal-most point 329A. In one embodiment, the first insertion tip 328A that is skewed outwardly relative to the longitudinal axis $A_{10}$ of the first leg 322A. The first leg 322A includes the distal barb 330A that extends inwardly toward the second leg 322B of the surgical fastener 320. The second leg 322B has a distal end 326B with the second insertion tip 328B having the distal-most point 329B. In one embodiment, the second insertion tip 328B is skewed outwardly relative to the longitudinal axis $A_{11}$ of the second leg 322B. The second leg 322B includes the barb 330B that extends inwardly toward the first leg 322A. The barbs 330A, 330B extend toward one another, oppose one another, and are aligned with one another adjacent the distal ends 326A, 326B of the respective first and second legs 322A, 322B. The central axis $A_{12}$ bisects the surgical fastener into a first half including the first leg 322A and a second half including the second leg 322B.

Figure 8F:
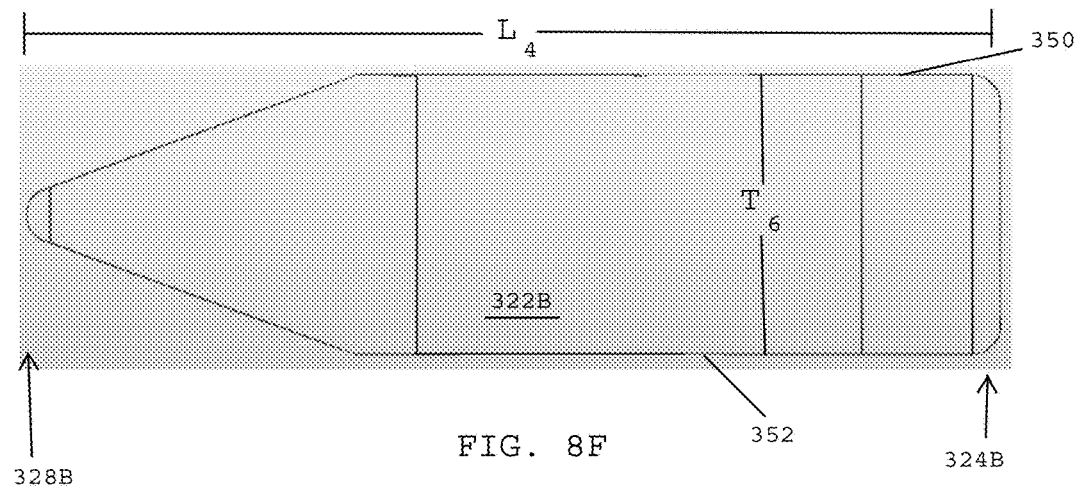

Referring to FIGS. 8E and 8F, in one embodiment, the surgical fastener 320 desirably includes a first major surface 350 that extends over a top side of the surgical fastener 320 and a second major surface 352 that extends over an underside of the surgical fastener 320. In one embodiment, the first major surface 350 is flat and extends over the bridge 338 and the first and second legs 322A, 322B on one side of the surgical fastener 320. In one embodiment, the second major surface 352 is also flat and extends over opposite sides of the bridge 338 and the first and second legs 322A, 322B.

Figure 9:
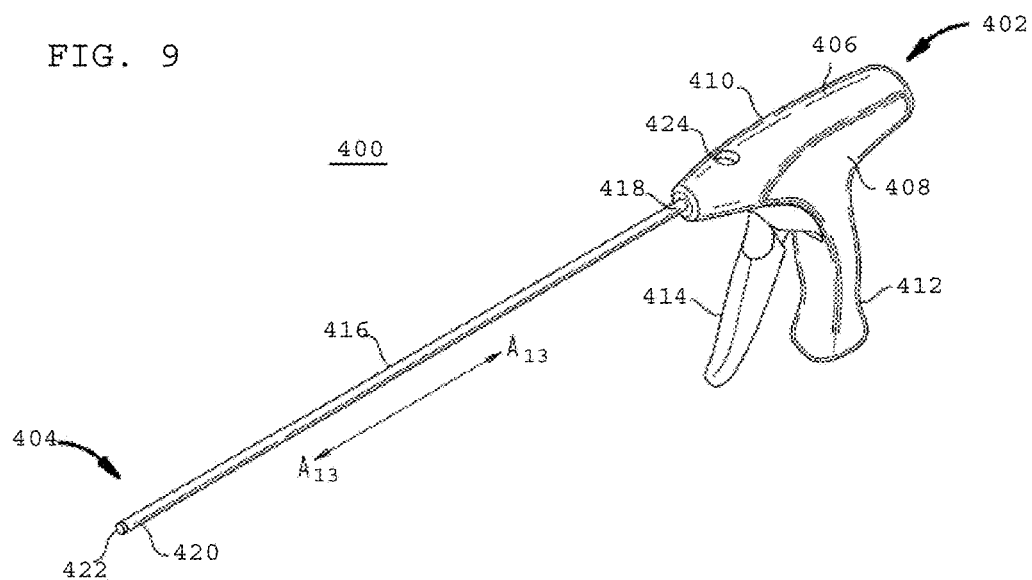
FIG. 9 shows an applicator instrument for dispensing surgical fasteners, in accordance with one embodiment.

Referring to FIG. 9, in one embodiment, an applicator instrument 400 for dispensing surgical fasteners has a proximal end 402 and a distal end 404. In one embodiment, the applicator instrument 400 is a multi-fire device that contains a plurality of surgical fasteners stored therein as disclosed in commonly assigned U.S. Pat. Nos. 8,579,920; 8,728,098; 8,728,099; 8,894,669; 8,920,439, and 9,055,945, the disclosures of which are hereby incorporated by reference herein. The applicator instrument 400 includes a housing 406 that contains a firing system for deploying the surgical fasteners. The housing 406 has a left cover 408 and a right cover 410. The left and right covers 408, 410 have lower ends forming a hand grip 412. The applicator instrument 400 preferably includes a trigger 414 that may be squeezed for dispensing the surgical fasteners from the distal end 404 of the instrument. In one embodiment, the applicator instrument 400 holds a plurality of surgical fasteners, whereby a single surgical fastener is dispensed from the distal end 404 of the applicator instrument each time the trigger 414 is squeezed. In one embodiment, the applicator instrument holds a plurality of surgical fasteners that are advanced toward the distal end of the outer tube 416 each time the trigger 414 is squeezed. The surgical fasteners preferably advance one position each time the trigger is squeezed.

In one embodiment, the applicator instrument 400 desirably includes an elongated outer shaft or tube 416 having a proximal end 418 coupled with a distal end of the housing 406 and a distal end 420 adapted to dispense the surgical fasteners. The distal-most end of the elongated outer tube 416 preferably has an end cap 422 secured thereto. The applicator instrument preferably has a longitudinal axis designated $A_{13}$ that extends between the proximal and distal ends 402, 404 thereof. The outer tube 416 desirably extends along the longitudinal axis $A_{13}$.

Figure 10:
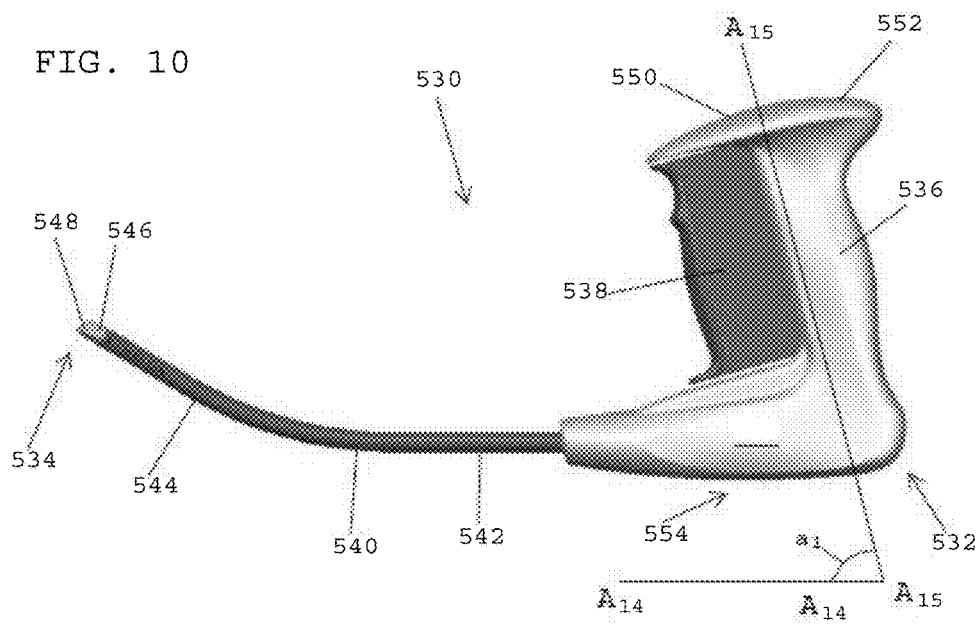
FIG. 10 shows an applicator instrument for dispensing surgical fasteners, in accordance with another embodiment.

Referring to FIG. 10, in one embodiment, an applicator instrument 530 for dispensing surgical fasteners has a proximal end 532, a distal end 534, and a longitudinal axis $A_{14}$ that extends between the proximal and distal ends. In one embodiment, the applicator instrument 530 is a multi-fire device that contains a plurality of surgical fasteners stored therein as disclosed in commonly assigned U.S. Pat. Nos. 8,579,920; 8,728,098; 8,728,099; 8,894,669; 8,920,439, and 9,055,945, the disclosures of which are hereby incorporated by reference herein. The applicator instrument 530 desirably includes a housing 535, a handle 536 extending upwardly from the housing, a trigger 538 mounted on the handle, and an elongated shaft 540 that extends distally from the housing 535. The elongated shaft 540 includes a first section 542 that extends along the longitudinal axis $A_{14}$ of the applicator instrument, and a second section 544 that is angled or curved relative to the first section 542.

In one embodiment, a cap 546 is secured to the distal end of the elongated shaft 540. The cap 546 preferably has a distal face 548 that slopes away from a lower distal edge of the cap and toward the proximal end 532 of the applicator instrument 530.

In one embodiment, the handle 536 includes an upper end 550 containing a counter 552 that indicates how many surgical fasteners have been dispensed and/or how many surgical fasteners remain loaded in the applicator instrument. In one embodiment, the counter 552 locks the applicator instrument from further use when the last surgical fastener has been dispensed. In one embodiment, the counter 552 is visible at the upper end 550 of the handle 536 to provide a visual indicator of how many of the surgical fasteners have been dispensed. The upper end of the handle defines the top of the applicator instrument 530. The housing 535 has a lower end 554 that defines the bottom of the applicator instrument 530.

In one embodiment, the handle 536 preferably leans toward the distal end 534 of the applicator instrument 530 to provide improved ergonomics for a surgeon so that the surgeon may maintain his/her elbow and wrist in a neutral position. In one embodiment, the handle 536 preferably extends along a longitudinal axis $A_{15}$ that defines an acute angle $\alpha 1$ with the longitudinal axis $A_{14}$ of the applicator instrument. In one embodiment, the angle $\alpha 1$ is about 70-80° and more preferably about 75°. During a surgical procedure, the lower end 554 of the housing 535 preferably faces toward a patient and the upper end 550 of the handle 536 preferably faces away from the patient.

In one embodiment, the applicator instrument 530 may be used for dispensing surgical fasteners during a surgical procedure such as an open hernia repair procedure. In one embodiment, the applicator instrument 50 has a plurality of surgical fasteners that are pre-loaded in the shaft 540 for being dispensed when the trigger 538 is squeezed. In one embodiment, a single surgical fastener is dispensed each time the trigger 538 is squeezed. In one embodiment, the applicator instrument 530 is used for dispensing surgical fasteners for the fixation of a mesh, such as a surgical mesh, to the soft tissue of a patient.

In one embodiment, during a surgical procedure, the angled second section 544 of the shaft 540 is inserted into a surgical opening. The lower end 554 of the housing 535 faces toward the patient and the upper end 50 of the handle 536 faces away from the patient. A surgeon may grasp the handle 536 and squeeze the trigger 538 for dispensing a surgical fastener from the distal end of the shaft 540. In one embodiment, the surgeon pulls the trigger 538 proximally (i.e. toward the proximal end 532 of the applicator instrument) for dispensing the surgical fasteners. The surgeon preferably applies counter pressure on the patient's tissue that opposes the distal end of the applicator instrument. In one embodiment, a single surgical fastener is dispensed each time the surgeon pulls the trigger 538 proximally, and the system finishes the firing cycle when the trigger is released for allowing the trigger to return distally.

Figure 11A:
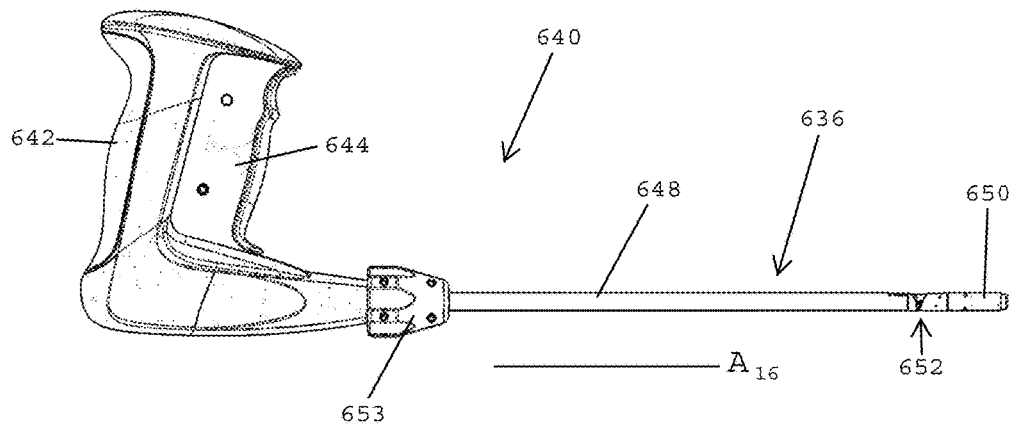
FIGS. 11A and 11B show an applicator instrument having an articulating shaft for dispensing surgical fasteners, in accordance with one embodiment.

Referring to FIG. 11A, in one embodiment, an applicator instrument 640 for dispensing surgical fasteners includes a handle 642 having a trigger 644, and an articulating shaft 646 with a proximal shaft section 648 and a distal shaft section 650 that articulates relative to the proximal shaft section. The distal shaft section 650 is moveable between a first position in which it extends along a longitudinal axis $A_{16}$ of the proximal shaft section 648 and an articulated configuration in which it is positioned at different angles relative to the longitudinal axis $A_{16}$ of the proximal shaft section 648. In one embodiment, a distal end of the proximal shaft section 648 is pivotally connected with a proximal end of the distal shaft section 650 via an articulating joint 652, which enables the distal shaft section 650 to articulate to different angles relative to the longitudinal axis $A_{16}$ of the proximal shaft section 648. The applicator instrument has an articulation control knob 653 that is rotated for changing the articulation angle between the distal shaft section 650 and the proximal shaft section 648. In one embodiment, rotating the articulation control knob in a first direction increases the articulation angle and rotating the articulation control knob in an opposite, second direction reduces the articulation angle. In one embodiment, the articulation control knob 653 may be used to set the distal shaft section 650 at an infinite number of angles between about 0-60. In one embodiment, the articulation angle may be as great as 80 degrees. In FIG. 11A, the articulating shaft 646 is straight so that the proximal shaft section 648 and the distal shaft section 650 both extend along the longitudinal axis $A_{16}$.

In one embodiment, the applicator instrument 640 is a multi-fire device that contains a plurality of surgical fasteners stored therein as disclosed in commonly assigned U.S. Pat. Nos. 8,579,920; 8,728,098; 8,728,099; 8,894,669; 8,920,439, and 9,055,945, the disclosures of which are hereby incorporated by reference herein. In one embodiment, the applicator instrument includes a plurality of surgical fasteners stored in series along the length of the articulating shaft 646. In one embodiment, the articulating shaft 646 includes a pair of flat stampings having tabbed features incorporated therein. One of the flat stampings is stationary for preventing the surgical fasteners from moving proximally within the articulating shaft 646. The other flat stamping cycles in distal and proximal directions each time the trigger 644 is squeezed and then released to facilitate incremental advancement of the surgical fasteners along the length of the articulating shaft 646. In one embodiment, the lead fastener is staged for firing proximal of the articulation joint 652. The firing rod pilots into the lead fastener and delivers it through the articulation and out of the surgical fastener dispensing window. Alternatively, the stampings are flexible so that the stampings may curve to conform to the angle of the articulating shaft while guiding the surgical fasteners along the path defined by the articulating shaft 646. In one embodiment, a single, lead surgical fastener is dispensed each time the trigger is pulled. During each trigger pull, each of the trailing surgical fasteners are advanced distally toward the distal end of the articulating shaft.

Figure 11B:
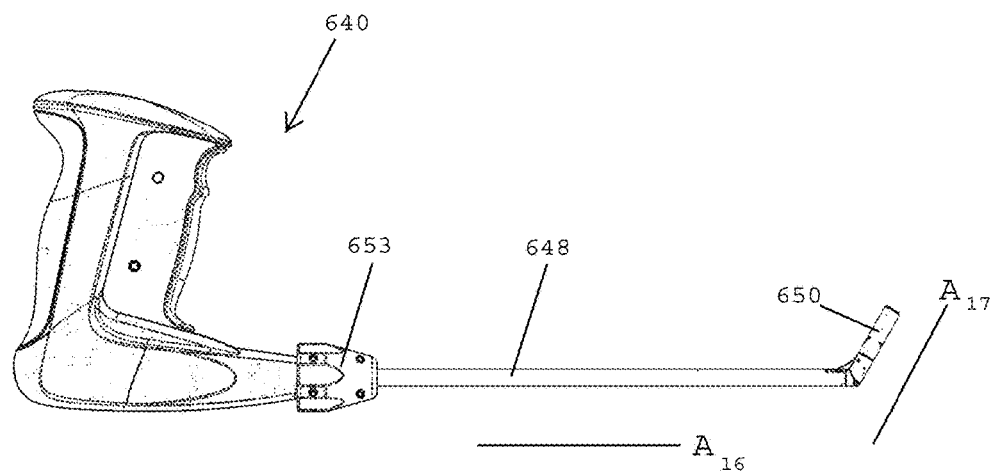

In one embodiment, the articulation control knob 653 is rotatable so that the distal shaft section 650 may be positioned at an infinite number of angles relative to the proximal shaft section 648. In FIG. 11A, the articulating shaft 646 is straight so that the distal shaft section 650 extends along the axis $A_{16}$ of the proximal shaft section 648. In FIG. 11B, the distal shaft section 650 extends along an axis $A_{17}$ that defines an angle $\alpha_2$ of about 45 degrees with the longitudinal axis $A_{16}$ of the proximal shaft section 648. In one embodiment, the distal shaft section 650 moves between 0-60 degrees relative to the longitudinal axis $A_{16}$ of the proximal shaft section 648. In one embodiment, the articulation control knob 653 may be used to change the articulation angle of the distal shaft section 650 to any angle between 0-80 degrees.

Figure 12A:
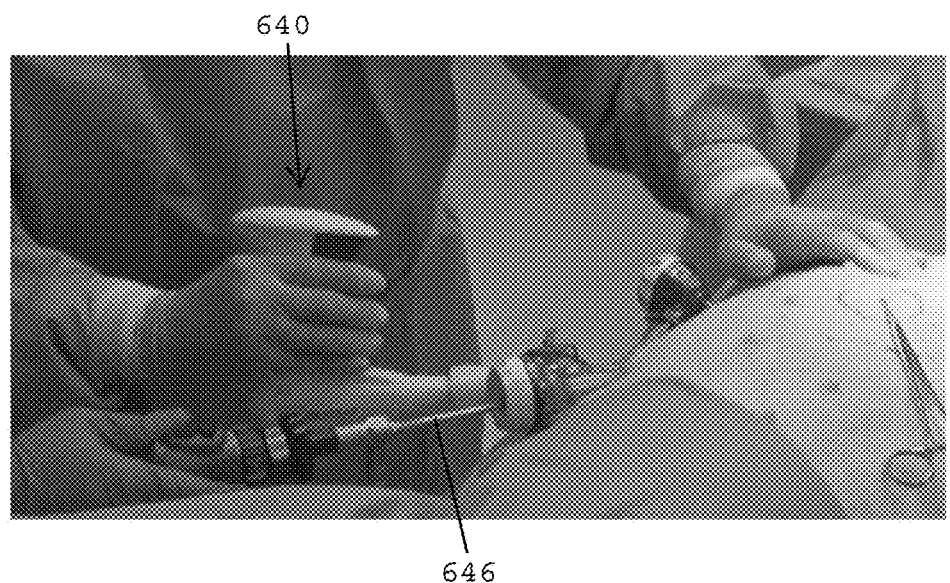
FIGS. 12A and 12B show a method of using an applicator instrument that dispenses surgical fasteners for securing a prosthetic device to tissue, in accordance with one embodiment.
Figure 12B:
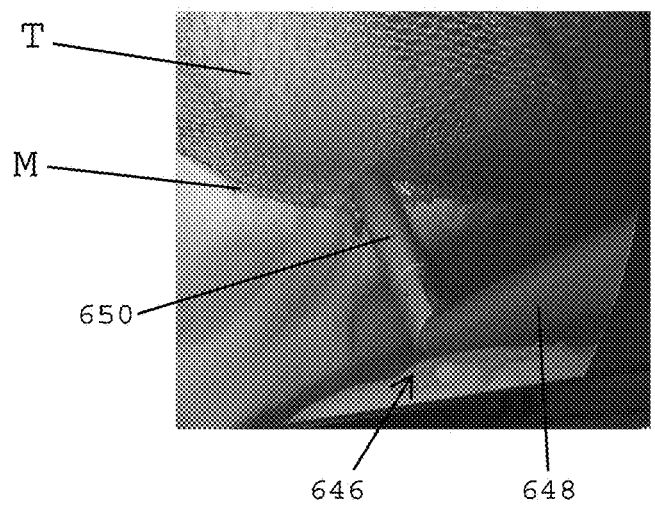

Referring to FIGS. 12A and 12B, during a surgical procedure, the articulating shaft 646 of the applicator instrument 640 is advanced through a cannula to a surgical site. The distal shaft section 650 may be articulated to an angle relative to the proximal shaft section 648 so that the distal end face of the distal shaft section is flush with a major surface of a surgical mesh M for securing the surgical mesh to underlying tissue T.

In one embodiment, a patient with a ventral or incisional hernia is prepared for a laparoscopic hernia repair procedure as set forth below. The patient is examined and the hernia location is identified using palpation or other methods. The patient is administered conventional general anesthesia in a conventional manner by induction and inhalation. A Veress needle is inserted into the abdominal cavity through the skin. A pneumoperitoneum of 8-15 mmHg is created. One 10 mm trocar is inserted in the left upper quadrant of the abdomen as far lateral as possible. A 30 degree laparoscopic camera is inserted through the trocar and the contents of the abdominal cavity are assessed. Two additional 5 mm trocars are placed caudal of the 10 mm port. Laparoscopic instruments are used to reduce the contents of hernia. The edges of the healthy fascia around the defect are examined and any attachments of viscera to the abdominal wall are divided to create a free space for fixation of the mesh. The size of the defect is assessed. In one embodiment, the defect may be primarily closed with sutures, if desired.

At this point in the procedure, the surgeon then prepares a mesh hernia patch. The mesh is sized to ensure adequate overlap beyond the margins of the defect on all sides. The mesh is rolled and inserted into the abdominal cavity through the 10 mm trocar. The mesh is unrolled and placed over the defect. Stay sutures may be placed through the mesh into the abdominal tissue as desired, i.e. at the four compass points of the mesh (North, South, East, West).

In one embodiment, an applicator instrument as disclosed herein, in the unarticulated configuration shown in FIG. 11A, is inserted through one of the 5 mm trocars. As desired, the surgeon may articulate the distal end of the applicator instrument (FIG. 11B) to improve the access of the applicator instrument to the mesh placed adjacent to the abdominal wall. The distal end of the applicator instrument may be used to manipulate the mesh and place the mesh in a desired location prior to being fixated. In one embodiment, the applicator instrument is placed in an articulated configuration manipulating the ipsilateral edge of the mesh nearest to the trocar sites. Regardless of whether the applicator instrument is articulated or unarticulated, the trigger of the applicator instrument is deployed (e.g., squeezed) to deliver surgical fasteners through the mesh and into the abdominal wall. The perimeter of the mesh is fixated using a plurality of surgical fasteners in a crown configuration. For each firing of the applicator instrument, the applicator instrument may be articulated or unarticulated, as appropriate for the target location of the fastener. In one embodiment, an inner crown of surgical fasteners may also be applied, if desired. In one embodiment, the surgeon may unarticulate and move the applicator instrument to one of the other trocars, if desired.

The mesh repair is inspected to ensure it is sufficiently fixated to the abdominal wall. The applicator instrument is unarticulated and removed from the trocar. The camera, laparoscopic instruments, and trocars are removed from the abdominal cavity. The trocar incisions may be closed using appropriate suturing or closure techniques. The patient is moved to a recovery room.

While the foregoing is directed to embodiments of the present invention, other and further embodiments of the invention may be devised without departing from the basic scope thereof, which is only limited by the scope of the claims that follow. For example, the present invention contemplates that any of the features shown in any of the embodiments described herein, or incorporated by reference herein, may be incorporated with any of the features shown in any of the other embodiments described herein, or incorporated by reference herein, and still fall within the scope of the present invention.

What is claimed is:

1. A surgical fastener comprising:
    a first leg including a proximal end, a distal end, a first longitudinal axis that extends between the proximal and distal ends of said first leg, and at least one barb extending from said first leg, wherein said first leg has a cross-sectional area that is greater at the proximal end than at the distal end;
    a second leg including a proximal end, a distal end, a second longitudinal axis that extends between the proximal and distal ends of said second leg, and at least one barb extending from said second leg, wherein said second leg has a cross-sectional area that is greater at the proximal end than at the distal end; and
    a bridge interconnecting the proximal ends of said first and second legs, wherein said bridge comprises a major surface that faces away from the distal ends of said first and second legs and a crown having a cruciform shape that extends proximally from said major surface of said bridge, wherein said crown having the cruciform shape includes a center section that is centered on said major surface of said bridge and first and second flanges that extend laterally from opposite sides of said center section.

2. The surgical fastener as claimed in claim 1, wherein said at least one barb on said first leg extends inwardly toward said second leg, and wherein said at least one barb on said second leg extends inwardly toward said first leg.

3. The surgical fastener as claimed in claim 2, wherein said at least one barb on said first leg comprises a first distal barb extending inwardly from the distal end of said first leg and a first proximal barb extending inwardly from a location on said first leg that is proximal to said first distal barb, and wherein said at least one barb on said second leg comprises a second distal barb extending inwardly from the distal end of said second leg and a second proximal barb extending inwardly from a location on said second leg that is proximal to said second distal barb.

4. The surgical fastener as claimed in claim 3, wherein a first distance between an inner tip of said first distal barb and an inner tip of said second distal barb is greater than a second distance between an inner tip of said first proximal barb and an inner tip of said second proximal barb.

5. The surgical fastener as claimed in claim 4, wherein said first and second distal barbs extend inwardly toward one another and are aligned with one another along the respective longitudinal axes of said first and second legs, and wherein said first and second proximal barbs extend inwardly toward one another and are aligned with one another along the respective longitudinal axes of said first and second legs.

6. The surgical fastener as claimed in claim 5, wherein the distal end of said first leg comprises a first insertion tip having a first distal piercing point and the distal end of said second leg comprises a second insertion tip having a second distal piercing point, and wherein said first and second insertion tips are asymmetrical.

7. The surgical fastener as claimed in claim 6, wherein said first distal barb extends inwardly from said first insertion tip and said second distal barb extends inwardly from said second insertion tip.

8. The surgical fastener as claimed in claim 7, wherein said first leg has a first outer wall that extends from a first end of said bridge to said first distal piercing point, and said second leg has a second outer wall that extends from a second end of said bridge to said second distal piercing point, and wherein the distance between said first and second outer walls defines a width of said surgical fastener that remains constant between the first and second ends of said bridge and said first and second distal piercing points.

9. The surgical fastener as claimed in claim 1, wherein said bridge extends along a proximal end of said surgical fastener, wherein said surgical fastener has a width that remains constant between said bridge and the distal ends of said first and second legs, and wherein said bridge has a length that defines the width of said surgical fastener at the proximal end of said surgical fastener.

10. The surgical fastener as claimed in claim 1, wherein said first leg tapers inwardly between the proximal and distal ends thereof, and said second leg tapers inwardly between the proximal and distal ends thereof.

11. The surgical fastener as claimed in claim 10, wherein the cross-sectional areas of said first and second legs at the proximal ends of said respective first and second legs define convex surfaces or cylindrical shapes adapted for plugging entrance holes created by the distal ends of said first and second legs so as to prevent or reduce bleeding from the entrance holes.

12. The surgical fastener as claimed in claim 1, wherein said major surface of said bridge comprises:
a first C-shaped section that surrounds said first flange;
a second C-shaped section that opposes said first C-shaped section and that surrounds said second flange.

13. A system for dispensing a surgical fastener, said system comprising:

said surgical fastener as claimed in claim 12; and
an insertion tool including a distal end having a distal face and first and second C-shaped projections on opposite ends of said distal face that oppose one another and that extend distally from said distal face, wherein said first C-shaped projection engages said first C-shaped section of said major face that surrounds said first flange of said crown, said second C-shaped projection engages said second C-shaped section of said major face that surrounds said second flange of said crown, and said center section of said crown is disposed between said first and second C-shaped projections.

14. The system as claimed in claim 13, wherein said crown defines a first height relative to said major surface of said bridge and said C-shaped projections define a second height relative to said distal face of said insertion tool that is greater than the first height, and wherein when said C-shaped projections of said insertion tool engage said first and second C-shaped sections of said major face, said distal face of said insertion tool is spaced away from said crown.

15. A surgical fastener comprising:
a first leg including a proximal end, a distal end, a first longitudinal axis that extends between the proximal and distal ends of said first leg, a first distal barb extending inwardly from the distal end of said first leg, and a first proximal barb extending inwardly from a location on said first leg that is proximal to said first distal barb;
a second leg including a proximal end, a distal end, a second longitudinal axis that extends between the proximal and distal ends of said second leg, a second distal barb extending inwardly from the distal end of said second leg, and a second proximal barb extending inwardly from a location on said second leg that is proximal to said second distal barb;
wherein a first distance between an inner tip of said first distal barb and an inner tip of said second distal barb is greater than a second distance between an inner tip of said first proximal barb and an inner tip of said second proximal barb;
a bridge interconnecting the proximal ends of said first and second legs, wherein said bridge comprises a major surface that faces away from the distal ends of said first and second legs and a crown having a cruciform shape that extends proximally from said major surface of said bridge, wherein said crown having the cruciform shape includes a center section that is centered on said major surface of said bridge and first and second flanges that extend laterally from opposite sides of said center section;
said first leg tapering inwardly between the proximal and distal ends thereof, wherein said first leg has a cross-sectional area that is greater at the proximal end than at the distal end; and
said second leg tapering inwardly between the proximal and distal ends thereof, wherein said second leg has a cross-sectional area that is greater at the proximal end than at the distal end.

16. The surgical fastener as claimed in claim 15, wherein said first and second distal barbs extend inwardly toward one another and are aligned with one another along the respective longitudinal axes of said first and second legs, and wherein said first and second proximal barbs extend inwardly toward one another and are aligned with one another along the respective longitudinal axes of said first and second legs.

17. The surgical fastener as claimed in claim 16, wherein the distal end of said first leg comprises a first insertion tip having a first distal piercing point, and the distal end of said second leg comprises a second insertion tip having a second distal piercing point, wherein said first and second insertion tips are asymmetrical relative to said respective longitudinal axes of said first and second legs, wherein said first leg has a first outer wall that extends from a first end of said bridge to said first distal piercing point, and said second leg has a second outer wall that extends from a second end of said bridge to said second distal piercing point, and wherein the distance between said first and second outer walls defines a width of said surgical fastener that remains constant between the first and second ends of said bridge and said first and second distal piercing points.

18. The surgical fastener as claimed in claim 17, wherein said major surface of said bridge includes a first C-shaped section that surrounds said first flange, and a second C-shaped section that opposes said first section and that surrounds said second flange.

19. A system for dispensing a surgical fastener, said system comprising:
  said surgical fastener as claimed in claim 18; and
  an insertion tool including a distal end having a distal face and first and second C-shaped projections on opposite ends of said distal face that oppose one another and that extend distally from said distal face, wherein said first C-shaped projection engages said first C-shaped section of said major face that surrounds said first flange of said crown, and said second C-shaped projection engages said second C-shaped section of said major face that surrounds said second flange of said crown.

* * * * *